United States Patent [19]

Sugimoto et al.

[11] Patent Number: 4,551,419
[45] Date of Patent: Nov. 5, 1985

[54] METHOD OF DEVELOPING SILVER HALIDE PHOTOGRAPHIC MATERIAL

[75] Inventors: Tadao Sugimoto; Hideo Ikeda; Koki Nakamura, all of Kanagawa, Japan

[73] Assignee: Fuji Photo Film Co., Ltd., Japan

[21] Appl. No.: 579,048

[22] Filed: Feb. 10, 1984

[30] Foreign Application Priority Data

Feb. 10, 1983 [JP] Japan .................................. 58-21269

[51] Int. Cl.$^4$ .............................................. G03C 5/26
[52] U.S. Cl. .................................... 430/445; 430/448; 430/603; 430/600; 430/611
[58] Field of Search ............... 430/603, 445, 448, 600, 430/611

[56] References Cited

U.S. PATENT DOCUMENTS

| 2,996,382 | 8/1961 | Luckey et al. | 430/502 |
| 3,021,215 | 2/1962 | Williams et al. | 430/603 |
| 3,178,282 | 4/1965 | Luckey et al. | 430/502 |
| 3,367,778 | 2/1968 | Berriman | 430/411 |
| 4,088,494 | 5/1978 | Tani | 430/600 |
| 4,150,993 | 4/1979 | Suga et al. | 430/409 |
| 4,309,501 | 1/1982 | Huguenard et al. | 430/603 |

FOREIGN PATENT DOCUMENTS 57-89749 6/1982 Japan .

Primary Examiner—Won H. Louie
Attorney, Agent, or Firm—Sughrue, Mion, Zinn, Macpeak, and Seas

[57] ABSTRACT

A silver halide photographic material which contains a light-sensitive silver halide emulsion and an internally fogged silver halide emulsion is development-processed in the presence of at least one compound selected from the group consisting of compounds represented by the general formulae (I) and (II) and at least one azaindene having a mercapto group to exhibit high photographic speed, high contrast and high maximum image density:

$$R_1\!-\!\{(R_3)_l\!X\}_n R_3'\!-\!R_2 \quad (I)$$

wherein $R_1$ and $R_2$ each represents a hydrogen atom, an aryl group, an aryl group, or a heterocyclic group; $R_3$ and $R_3'$ each represents an alkylene group, an arylene group, a heterocyclic group; X presents

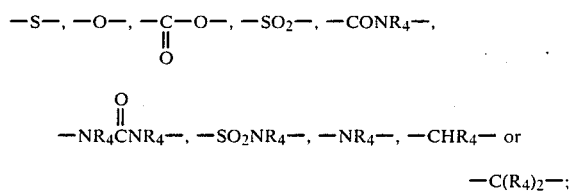

$R_4$ represents a hydrogen atom or $-\!R_5\!-\!Y\}_m R_5'\!-\!R_6$; $R_5$ and $R_5'$ have the same meanings as $R_3$ and $R_3'$; $R_6$ has the same meaning as $R_1$ and $R_2$; Y represents

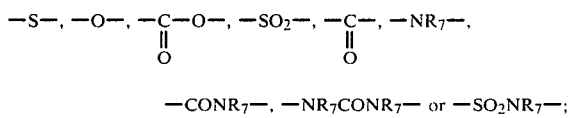

$R_7$ has the same meaning as $R_1$ and $R_2$; l represents 0 or 1, n represents an integer of 1 to 110, and m represents an integer of 0 to 10, and at least one X therein must be a sulfur atom:

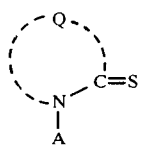

(II)

wherein Q represents atoms necessary to form a heterocyclic ring, and A represents an alkyl group, or an aryl group.

26 Claims, No Drawings

METHOD OF DEVELOPING SILVER HALIDE PHOTOGRAPHIC MATERIAL

FIELD OF THE INVENTION

The present invention relates to a novel silver halide photographic material and more particularly, to a high speed silver halide photographic material which provides images of high contrast and high maximum density.

BACKGROUND OF THE INVENTION

With respect to photographic images made up of silver grains, the ratio of optical density of the image to a per unit area amount of silver which constitutes the image is generally called covering power. This ratio is employed as a measure for estimating the optical efficiency of the silver making up the image. The covering power of a silver halide photographic light-sensitive layer is, in general, higher the smaller the size of the silver halide grains, and decreases with increasing grain size. On the other hand, the photographic speed of a silver halide emulsion layer generally increases the larger the size of the silver halide grains. Consequently, silver halide emulsions having large grain sizes are employed for photographic materials having high photographic speeds. Accordingly, photographic light-sensitive materials having high photographic speeds require a large per unit area amount of silver for attaining some definite height of image density. Namely, if one intends the photographic material to have both high speed and required maximum image density, one must incorporate light-sensitive silver salts into the photographic material in a larger amount per unit area thereof. This is the real state of conventional photographic materials having high speeds.

One attempts at improving the covering power while maintaining high speed is a technique of adding various kinds of polymers to coarse-grained silver halide emulsions having high photographic speeds. This technique is described in British Pat. Nos. 1,048,057 and 1,039,471; and U.S. Pat. Nos. 3,043,697 and 3,446,618. The use of each of these polymers has some, though not a wholly satisfactory, effect on heightening the covering power. However, they lower the strength of coated films. Therefore, such a technique is unacceptable. This is because if photographic materials containing coated films having little strength are processed, especially using an automatic developing machine which is prevailingly employed at present, part of the gelatin contained therein is eluted with the developing solution or the fixing solution and adheres to the conveyor rollers of the automatic developing machine and further, is transferred onto photographic materials processed later, staining the photographic images produced thereon.

On the other hand, U.S. Pat. Nos. 2,996,382 and 3,178,282 describe that if silver halide photographic materials having a coarse-grained silver halide emulsion of the kind which forms latent images at the surface predominantly and a fine-grained silver halide emulsions having fogging nuclei inside the grains in the same layer or in the adjacent layers separately are employed, photographic images of high contrast and high covering power can be obtained at high speeds.

However, sufficiently high speed, density and contrast still cannot be acquired by using such a method. In addition, that method suffers from the disadvantages that it requires a long time for effecting development in the usual low temperature processing, whereas in the usual high temperature rapid processing it cannot exhibit the desired effects.

In order to improve the above-described disadvantages, a technique of incorporating a thioether compound (e.g. $C_6H_{13}OCOCH_2CH_2SCH_2CH_2SCH_2CH_2OCOC_6H_{13}$) or a nitrogen-containing heterocyclic compound having a thioketone group into a photographic material having a light-sensitive silver halide emulsion and an internally fogged silver halide emulsion is proposed by published unexamined Japanese Patent Application 89749/82. However, satisfactory improvement upon the above-described disadvantages cannot be made with such a method.

Moreover, we have found previously (disclosed in Japanese Patent Application No. 22372/83) that such a compound as to be represented by the general formula (I) described hereinafter wherein both $R_1$ and $R_2$ are at least one hydroxyl group-containing alkyl, aryl or heterocyclic groups is effective for the improvement upon the above-described disadvantages, but its effect is insufficient. More specifically, it cannot contribute to acquirement of sufficiently high photographic speed, contrast and maximum density, especially when the bromine ion concentration in the developing solution is low.

On the other hand, we have also found and disclosed in Japanese Patent Application No. 210498/82 that the defects inherent in the technique described in U.S. Pat. Nos. 2,996,382 and 3,178,282; that is to say, a tendency to cause developmental fog and a tendency to cause uneven stains in a photographic material, can be lessened by the use of at least one mercapto group-containing tetrazaindenes, at least one mercapto group-containing purines, at least one mercapto group-containing triazaindenes or at least one mercapto group-containing pentazaindenes. However, all the capability of this technique cannot satisfy to the full the above-described requirements of a photographic material, that is, acquirements of sufficiently high photographic speed, contrast and maximum density. More specifically, with this technique desired effects cannot be produced to a satisfactory extent, especially under the condition of a low bromine ion concentration in the developing solution.

Since the bromine ion concentration in the developing solution varies with the number of processed films in the development using an automatic developing machine, which is usually employed on the market, and during development by hand, it is important to produce photographic images having unchanged properties, irrespective of the change of the bromine ion concentration.

SUMMARY OF THE INVENTION

Therefore, an object of the present invention is to provide a silver halide photographic material and a method for development-processing thereof which enables production of photographic images of high maximum density with a high photographic speed and high contrast.

Another object of the present invention is to provide a silver halide photographic material and a method for development-processing thereof which can provide photographic images of high maximum density with satisfactory high photographic speed and contrast even under the condition that a developing solution used has a low bromine ion concentration.

As the result of many studies on attaining such objects, is has now been found that the above-described problems are dissolved by using the following photographic material and processing method.

That is, the present invention is a method for development of a silver halide photographic material containing a light-sensitive silver halide emulsion and an internally fogged silver halide emulsion, which method comprises developing the silver halide photographic material in the presence of at least one compound represented by the general formulae (I) and (II) and at least one azaindene containing a mercapto group:

$$R_1\text{—}(R_3)_l X\text{—}_n R_3{'}\text{—}R_2 \tag{I}$$

wherein $R_1$ and $R_2$ each represents a hydrogen atom, a substituted or unsubstituted alkyl group, a substituted or unsubstituted aryl group, or a substituted or unsubstituted heterocyclic group; $R_3$ and $R_3{'}$ each represents a substituted or unsubstituted alkylene group, a substituted or unsubstituted arylene group, a substituted or unsubstituted heterocyclic group, or a combination thereof; X represents

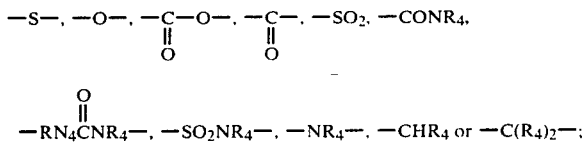

$R_4$ represents a hydrogen atom or $+R_5\text{—}Y\frac{}{m}R_5{'}\text{—}R_6$; $R_5$ and $R_5{'}$ have the same meanings as $R_3$ and $R_3{'}$; $R_6$ has the same meaning as $R_1$ or $R_2$; Y represents

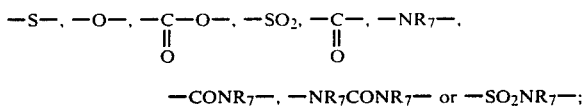

$R_7$ has the same meaning as $R_1$ or $R_2$; and l represents 0 or 1, n represents an integer of 1 to 110, and m represents an integer of 0 to 10, wherein when m and n each is not less than 2, that is, the moiety containing $R_3$ and X and the moiety containing $R_5$ and Y are repeating units, these groups may be different in every repeating unit respectively and that, at least one X therein must be a sulfur atom:

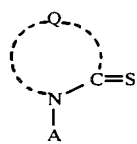

wherein Q represents atoms necessary to form a heterocyclic ring which may be substituted, and A represents a substituted or unsubstituted alkyl group, or a substituted or unsubstituted aryl group.

DETAILED DESCRIPTION OF THE INVENTION

The marvel is that quite unexpectedly high photographic speed, contrast and maximum density can be gained by the combined use of at least one compound represented by the general formula (I) or (II) with an azaindene having a mercapto group.

It is advisable to incorporate compound represented by the general formulae (I) or (II) into a photographic material from the standpoint of improving the preservability of a developing solution, though compounds represented by the formulae (I) or (II) and an azaindene having a mercapto group may be added to a developing solution. Further, it is more preferable to incorporate at least one compound represented by the general formula (I) or (II) and azaindenes having mercapto groups into a photographic material in that a developing solution can be employed with other photographic materials in addition to improvement upon preservability of the developing solution.

In the present invention, the expression "a low bromine ion concentration in the developing solution" is intended to include concentrations not higher than, e.g., 5 g/l based on potassium bromide.

The general formula (I) is illustrated in detail below.

The alkyl group represented by $R_1$ and $R_2$ in the general formula (I) include a straight chain, branched chain or cyclic alkyl group such as —$CH_3$, —$CH_2CH_3$, —$CH_2CH_2CH_3$,

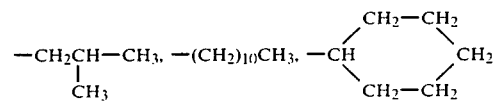

and so on, and the number of carbon atoms contained in the alkyl group is preferably 1 to 20 and more preferably 1 to 12. Suitable examples of the aryl group for $R_1$ and $R_2$ include

and so on, and a preferable number of carbon atoms contained in the aryl group is 6 to 20.

Suitable examples of the heterocyclic ring for $R_1$ and $R_2$ include saturated and unsaturated cyclic (e.g., 4- to 6-membered) ring containing sulfur, nitrogen and/or oxygen atoms, such as

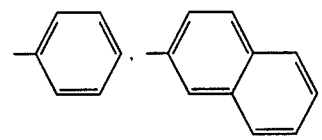

imidazole, benzimidazle, oxazole, benzoxazole, thiazole, benzotriazole, triazole, benzotriazole, pyridine, pyrazine, quinoline, triazine, tetrazole, azaindenes (e.g., triazaindene, tetrazaindene, pentazaindene, etc.), purine, thiadiazole, oxadiazole and so on.

In addition, substituents represented by $R_1$ or $R_2$ may be substituted with a hydroxyl group, a halogen atom (e.g., chlorine, bromine, etc.), an alkyl group (e.g., methyl, ethyl, butyl, isopropy, etc., preferably one which contains 1 to 10 carbon atoms), an aryl group (e.g., phenyl, naphthyl, etc., preferably one which contains 6 to 15 carbon atoms), an amino group, mono- or di-alkyl substituted amino group wherein the alkyl moiety contains 1-6 carbon atoms (e.g., —NHCH$_3$, —N(C$_2$H$_5$)$_2$, etc.), —COOH, —COOM, —SO$_3$M (M: Na, K, etc.), etc.

In particular, the present invention has a more desirable effect when at least one of R$_1$ and R$_2$ is substituted with at least one hydroxy groups. Among those alkyl groups, the alkyl group is more effective the larger the hydroxyl group attached thereto in number.

Examples of the alkylene group represented by R$_3$ and R$_3'$ of the general formula (I) include alkylene group preferably having 1-5 carbon atoms. Examples of the arylene group represented by R$_3$ and R$_3'$ include

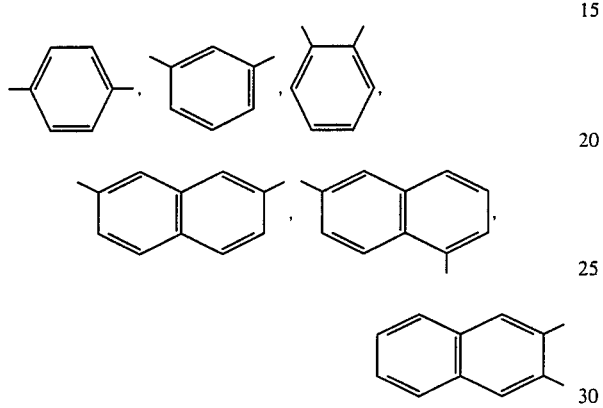

and so on. Examples of the hetero ring nucleus represented by R$_3$ or R$_3'$ include

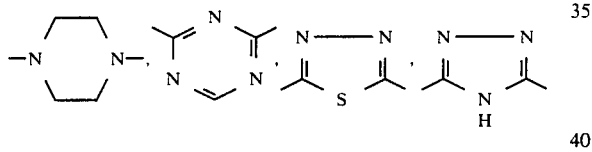

and so on. Further, R$_3$ and R$_3'$ may be substituted in analogy with R$_1$ and R$_2$. Especially good results can be obtained when R$_3$ and R$_3'$ are alkylene groups (which may be substituted).

Preferable examples of the moiety represented by X include —S—, —O—, —CONH— and those which have H as R$_4$. Especially favorable moieties are —S—, —O—, —CONH—. Preferable n is an integer of 1 to 10, particularly 1 to 5, though it may range from 1 to 110. In case that R$_4$ represents —R$_5$—Y$\}_m$R$_5'$—R$_6$, m represents 0 to 10, preferably 0 to 5, and preferable examples of the moiety represented by Y include —S—, —O— and —CONH—.

On the occasion that n represents an integer of 2 or more in the moiety R$_3$—X$_n$, the expression "R$_3$ and X need not be the same in every parenthesis in a repetition of the moieties" means that when —R$_3$—X$\}_n$ is rewritten by an alternative expression, (R$_3$)$_1$—X—(R$_3$)$_2$—X$_2$—(R$_3$)$_3$—X$_3$— ... (R$_3$)$_n$—X$_n$, (R$_3$)$_1$ to (R$_3$)$_n$ and X$_1$ to X$_n$ respectively may be different from one another. For instance, —S—CH$_2$—S—, —CH$_2$—S—CH$_2$—S—, —S—CH$_2$CH$_2$—S—, —S—CH$_2$CH$_2$—S—CH$_2$CH$_2$—S—, —S—CH$_2$CH$_2$—O—CH$_2$CH$_2$—S—, —S—CH$_2$CH$_2$—CONH—CH$_2$—CONH—CH$_2$CH$_2$—S—, —S—CH$_2$CH$_2$CH$_2$—NHCONH—, —S—CH$_2$CH$_2$—CO$_2$—CH$_2$CH$_2$—S—, —S—CH$_2$CH$_2$—SO$_2$—NH— and the like may be included in examples of the moiety —R$_3$—X$\}_n$.

The same may be said for the moiety —R$_5$—Y$\}_m$.

Especially advantageous compounds among those represented by the general formula (I) are those containing not more than 20 carbon atoms in all.

Specific examples of compounds represented by the general formula (I) of the present invention are illustrated below.

| | |
|---|---|
| HOC$_2$H$_4$SC$_6$H$_{13}$ | I-1 |
| HOC$_2$H$_4$SC$_8$H$_{17}$ | I-2 |
| HOC$_2$H$_4$SC$_2$H$_4$CO$_2$C$_2$H$_5$ | I-3 |
| HOC$_2$H$_4$SC$_2$H$_4$CO$_2$C$_4$H$_9$(t) | I-4 |
| HOC$_2$H$_4$SCH$_2$CO$_2$C$_2$H$_5$ | I-5 |

I-6

HOC$_2$H$_4$S—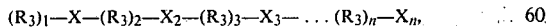

I-7

C$_2$H$_5$SC$_2$H$_4$NHC(O)NHC$_2$H$_4$C(O)OC$_2$H$_4$OC(O)NHC$_2$H$_5$

I-8

C$_6$H$_{13}$OC(O)C$_2$H$_4$SC$_2$H$_4$SC$_2$H$_4$C(O)OC$_6$H$_{13}$

I-9

CH$_4$H$_9$S(C$_2$H$_4$O)$_{66}$C(O)CH$_2$H$_4$COOH

| | |
|---|---|
| C$_2$H$_5$SC$_8$H$_{17}$ | I-10 |
| HOCH$_2$CH$_2$SCH$_2$CH$_2$OCH$_2$CH$_2$SCH$_2$CH$_2$OH | I-11 |
| HOCH$_2$CHCH$_2$SCH$_2$CH$_2$SCH$_2$CHCH$_2$OH<br>     \|                                    \|<br>    OH                                  OH | I-12 |
| HOCH$_2$CH$_2$SCH$_2$SCH$_2$CH$_2$OH | I-13 |
| HOCH$_2$CH$_2$SCH$_2$CH$_2$CONHCH$_2$NHCOCH$_2$CH$_2$SCH$_2$CH$_2$OH | I-14 |
| HOCH$_2$CH$_2$SCH$_2$CH$_2$SCH$_2$CH$_2$SCH$_2$CH$_2$OH | I-15 |
| HOCH$_2$CHCH$_2$SCH$_2$CH$_2$SCH$_2$CH$_2$SCH$_2$CHCH$_2$OH<br>     \|                                                   \|<br>    OH                                                 OH | I-16 |
| HOCH$_2$CH$_2$SCH$_2$CH$_2$SCH$_2$CH$_2$OH | I-17 |
| HOCH$_2$CH$_2$SCH$_2$CH$_2$OH | I-18 |
| HOCH$_2$CH$_2$SCH$_2$CH$_2$NHCONHCH$_2$CH$_2$OH | I-19 |

I-20

HOCH$_2$CHCH$_2$SCH$_2$CH$_2$C(O)CH$_2$CH$_2$SCH$_2$CHCH$_2$OH
     |                                                    |
    OH                                                  OH

| | |
|---|---|
| HOCH$_2$CH$_2$SCH$_2$CH$_2$SO$_2$NHCH$_2$CH$_2$OH | I-21 |
| CH$_3$CHCH$_2$SCH$_2$CH$_2$OH<br>     \|<br>    OH | I-22 |
|     CH$_3$  CH$_3$<br>      \|       \|<br>HO(CH$_2$)$_2$S—CH—CH—SCH$_2$CH$_2$OH | I-23 |

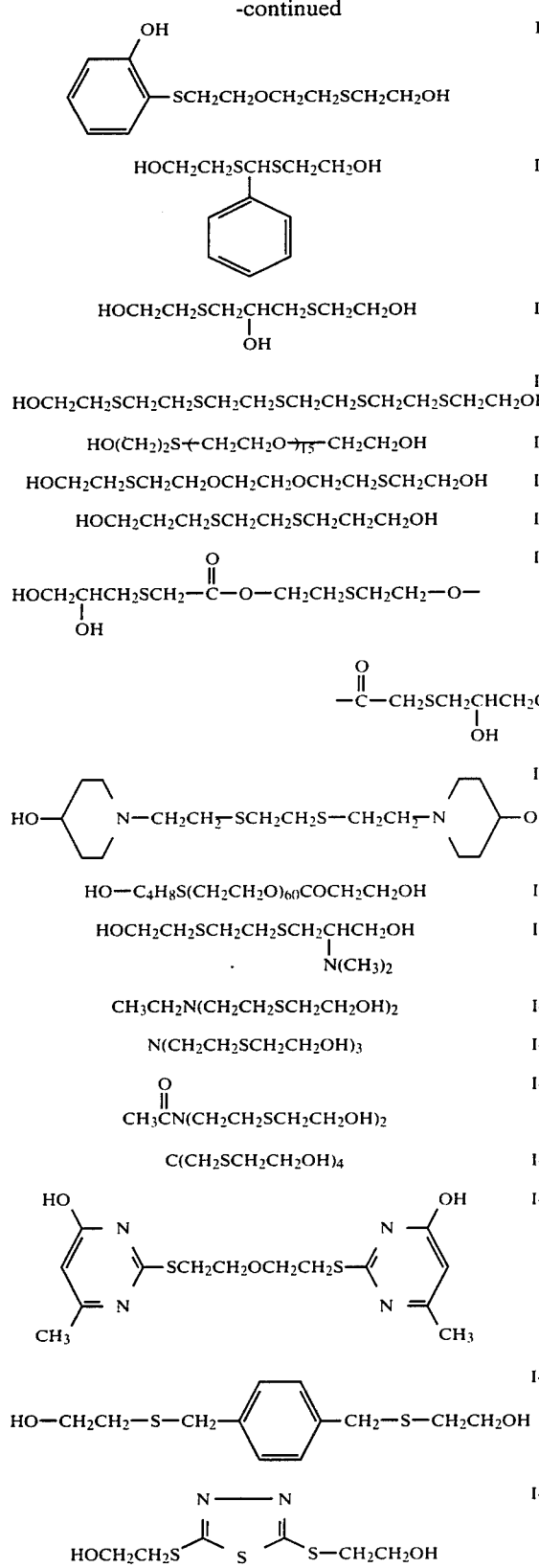

The compounds represented by the general formula (I) can be synthesized with ease using or being based on the methods described in Shin Jikken Kagaku Koza 14 [III] (compiled by Japan Chemical Society), pp. 1715–1726, Maruzen, Tokyo (1978). On the other hand, symmetric or asymmetric sulfides can be synthesized with high yields by reacting thiol compounds with alkyl halides in the presence of a base. Examples of these reactions are described in detail in the following literatures: i.e., Chem. Ber., 82, 426 (1949); J. Chem. Soc., 121, 2882 (1922); Synthesis, 1974, 565; J.A.C.S., 42, 2385 (1920); ditto, 74, 828 (1952); ditto, 72, 2856 (1950); ditto, 46, 961 (1924); ditto, 70, 1381 (1948); and so on. Compounds from which X (containing $R_4$) is derived may be synthesized on the basis of the methods described in Shin Jikken Kagaku Koza 14-[II], [III], [IV].

Typical synthesis examples of the compounds represented by the general formuia (I) are described in detail below. The compounds, other than those exemplified below, can be synthesized with ease according to the following processes or the methods illustrated in the foregoing literatures.

Synthesis Example I-1: Synthesis of
3,6-Dithia-1,8-octanediol
($HOCH_2CH_2SCH_2CH_2SCH_2CH_2OH$)

In an ice bath, 25 g of dithioglycol was stirred and thereto, was added dropwise 1.1 equivalent of a methanol solution of sodium methoxide. Further, 44 g of ethylene chlorohydrin was added dropwise thereto. After the conclusion of the dropwise addition, the reaction mixture was allowed to stand for 10 hours at a room temperature. Then, sodium chloride deposited was removed by filtration, and the resulting filtrate was concentrated. The thus obtained white crystals were recrystallized from acetone. Melting Point 65° C., Yield 25 g.

Synthesis Example I-2: Synthesis of
3,12-Dithia-6,9-dioxa-1,14-tetradecanediol
($HOCH_2CH_2SCH_2CH_2OCH_2CH_2OCH_2CH_2SCH_2C$-$H_2OH$)

(1) Synthesis of 3,6-Dioxo-1,8-dichlorooctane

In an oce bath, 408 g of thionyl chloride was added to 283 g of triethylene glycol in such a condition that an inside temperature of the reaction system was maintained at 44°–45° C. Thereto, 7 g of pyridine was, then, added and the resulting mixture was heated at 140°–145° C. for 1 hour. The thus obtained product was purified by distillation.

Yield 180 g.

(2) Synthesis of
3,12-Dithia-6,9-dioxa-1,14-tetradecanediol

A mixture of 37.4 g of 3,6-dioxo-1,8-dichlorooctane obtained above, 31.2 g of 2-mercaptoethanol, 21.2 g of sodium carbonate and 200 ml of 50% ethanol was refluxed for 20 hours. The product was distilled under vacuum. bp (at 1.5 mmHg) 215°–225° C., Yield 7 g.

Synthesis Example I-3: Synthesis of
3,9-Dithia-6-oxa-1,11-undecanediol
($HOCH_2CH_2SCH_2CH_2OCH_2CH_2SCH_2CH_2OH$)

In 50% ethanol (containing 50% of water), 15.6 g of 2-mercaptoethanol, 14.3 g of bis(2-chloroethyl)ether and 10.6 g of sodium carbonate were dissolved, and the resulting solution was refluxed for 20 hours. After removal of the solvent by distillation under reduced pressure, the reaction product was extracted with hot absolute ethanol and ethyl acetate. The desired compound was obtained by distilling the extract.

bp (at 1.0 mmHg) 181° C.

Synthesis Example I-4: Synthesis of
4,7-Dithia-1,10-decanediol
(HOCH$_2$CH$_2$CH$_2$SCH$_2$CH$_2$SCH$_2$CH$_2$CH$_2$OH)

To 300 ml of absolute methanol, was added 12.2 g of metallic sodium. To the resulting solution which was being stirred in an ice bath, was added dropwise 25 g of dithioglycol. After the dropwise addition, the stirring was continued for additional 30 minutes in the ice bath. Then, 52 g of 3-chloro-1-propanol was further added dropwise. At the conclusion of the dropwise addition, the temperature of the reaction system was raised to a room temperature, and the reaction system was allowed to stand for 10 hours at the room temperature. The thus produced sodium chloride was removed by filtration under reduced pressure, and the resulting filtrate was concentrated. Crystals thus obtained were recrystallized from acetone. Melting Point 52° C., Yield 20 g.

Synthesis Example I-5: Synthesis of
3,5-Dithia-1,7-heptanediol
(HOCH$_2$CH$_2$SCH$_2$SCH$_2$CH$_2$OH)

In an ice bath, 39 g of 2-mercaptoethanol was dissolved in methanol and thereto, was slowly added dropwise 100 g of sodium methoxide (as a 28% methanol solution). Thirty minutes later, 43 g of dibromoethane was further added dropwise taking 1 hour. After the conclusion of the dropwise addition, the reaction system was heated up to a room temperature, and allowed to stand for 15 hours at that temperature. Sodium chloride thus deposited was removed by filtration, and the resulting filtrate was concentrated. The product was purified by distillation.

bp (at 0.25 mmHg) 133° C.

Synthesis Example I-6: Synthesis of
3-Thia-1,5-pentanediol (HOCH$_2$CH$_2$SCH$_2$CH$_2$OH)

In an ice bath, 39 g of 2-mercaptoethanol was dissolved in methanol and thereto, was slowly added dropwise 100 g of sodium methoxide (as a 28% methanol solution). After 30 minutes' stirring, 41 g of ethylene chlorohydrin was further added sloly dropwise. At the conclusion of the dropwise addition, the temperature of the reaction system was raised to room temperature, and allowed to stand overnight. The thus deposited sodium chloride was removed by filtration, and the resulting filtrate was concentrated. The desired compound was obtained by distillation of the concentrate, bp (at 20 mmHg) 165° C., Yield 42 g.

General formula (II) is illustrated in detail below.

Suitable examples of the heterocyclic ring formed by Q in the foregoing general formula (II) include thiazoline-2-thione rings, benzothiazoline-2-thione rings, thiazolidine-2-thione rings, imidazolidine-2-thione rings, selenazolidine-2-thione rings, 1,3,4-thiadiazoline-2-thione rings, 1,3,4-selenadiazoline-2-thione rings, 4-selenazoline-2-thione rings, 1,2-dihydropyridine-2-thione rings, benzoxazoline-2-thione rings, benzimidazoline-2-thione rings, benzoselenazoline-2-thione rings, 1,2-dihydroquinoline-2-thione rings, rhodanine rings and so on. Among these rings, thiaazoline-2-thione rings, benzothiazoline-2-thione rings, thiazolidine-2-thione rings, 1,3,4-thiadiazoline-2-thione rings and rhodanine rings are of greater advantage.

Examples of substituents of the heterocyclic rings include the same groups as the alkyl or aryl groups represented by R$_1$ and R$_2$ in the general formula (I) and an alkenyl group and an aralkenyl group such as benzylidene group.

Suitable examples of the alkyl group represented by A include unsubstituted ones which contain 1 to 10 carbon atoms and those substituted with a hydroxyl group, an aryl group, a morpholino group, alkyl thio group preferably having 1 to 4 carbon atoms and those which are substituted with a hydroxy group or so on, such as methyl, ethy, propyl, hexyl, decyl, hydroxyethyl, benzyl, morpholinoethyl, etc. On the other hand, suitable examples of the aryl group represented by A include unsubstituted ones and those substituted with an alkyl group, preferably having 1 to 4 carbon atoms, an alkoxy group preferably having 1 to 4 carbon atoms, an alkylthio group preferably having 1 to 4 carbon atoms and the group substituted with a hydroxy group, a halogen atom or so on, such as 4-methoxyphenol, 4-chlorophenyl, etc.

Now, specific examples of compounds represented by the general formula (II) of the present invention are illustrated below.

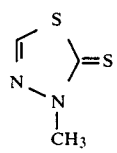

II-1

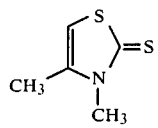

II-2

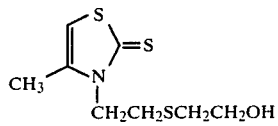

II-3

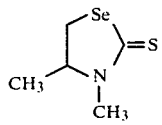

II-4

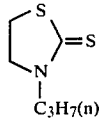

II-5

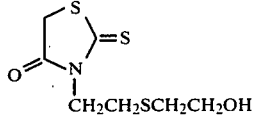

II-6

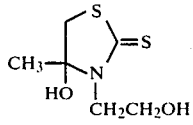

II-7

-continued

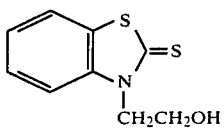

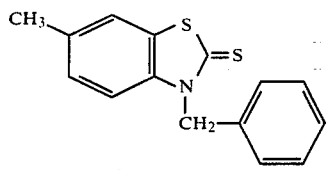

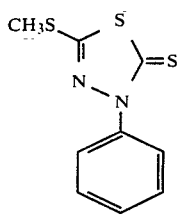

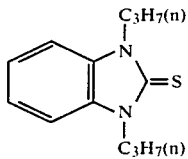

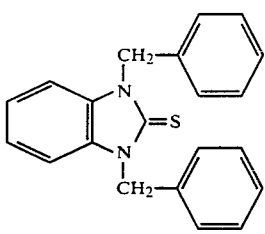

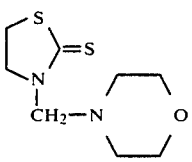

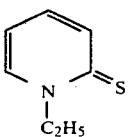

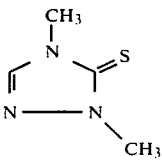

II-8

II-9

II-10

II-11

II-12

II-13

II-14

II-15

-continued

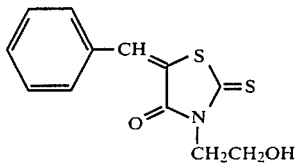

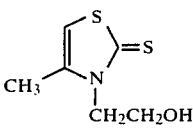

II-16

II-17

The compounds represented by the general formula (II) are known ones, and can be synthesized with ease or are available on the market. A synthesis example of the presentative of these compounds is illustrated in detail below. Also, compounds other than the representative ones can be synthesized with ease in the same manner as in the following example.

Synthesis Example II-1: Synthesis of 3-(2-(2-hydroxyethyl)-thioethyl)-4-methyl-4-thiazoline-2-thione

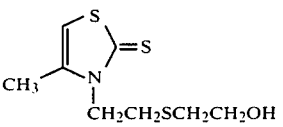

(1)

(a) Synthesis of 2-(2-hydroxyethylthio)ethylamine (2)

In 500 ml of a methanol 39 g of 2-mercaptoethanol was dissolved and 43 g of ethyleneimine was added dropwise slowly to the resulting mixture having a temperature of 0° C. Thereafter, it was permitted to stand overnight at a room temperature. Then, methanol was distilled away under reduced pressure. Thus, (2) was obtained in an oily condition. (2) was submitted to the next reaction without receiving any purification.

(b) Synthesis of 3-(2-(2-hydroxyethyl)thioethyl)-4-methyl-4-thiazoline-2-thione (1)

In 500 ml of ethanol, 24.2 g of (2) and 24.7 ml of triethylamine were dissolved and cooled to 0° C. Thereto, 16.8 g of carbon disulfide was added dropwise. The resulting mixture was allowed to stand for 2 hours at a room temperature and further, for an additional 30 minutes at 50° C. to conduct the reaction. Then, the reaction mixture was cooled to 0° C. again. Thereto, 19.4 g of chloroacetone was added dropwise. The reaction was run by keeping the temperature of the reaction-system at a room temperature for 1 hour and further, at 40° C. for an additional 2 hours. At the conclusion of the reaction, the solvent was removed by distillation under reduced pressure, and water was added to the residue. The reaction product was extracted with ethyl acetate, washed with water three times, and dried over anhydrous sodium sulfate. Upon the removal of ethyl acetate from the extract by distillation, (1) was obtained as an oily sub stance.

In the present invention, it is particularly preferable to employ the compounds represented by the general formula (I).

Preferable examples of mercapto group-containing azaindenes used in the present invention include tetrazaindenes containing at least one mercapto group (including purines containing at least one mercapto group), triazaindenes containing at least one mercapto group and pentazaindenes containing at least one mercapto group.

Of mercapto group-containing azaindenes, those having the following general formula (IIIa) to (IIIf) are more advantageously employed.

That is, tetrazaindenes having the general formula (IIIa) to (IIId) (purines have the general formula (IIId)), triazaindenes having the general formula (IIIe) and pentazaindenes having the general formula (IIIf) are preferably employed.

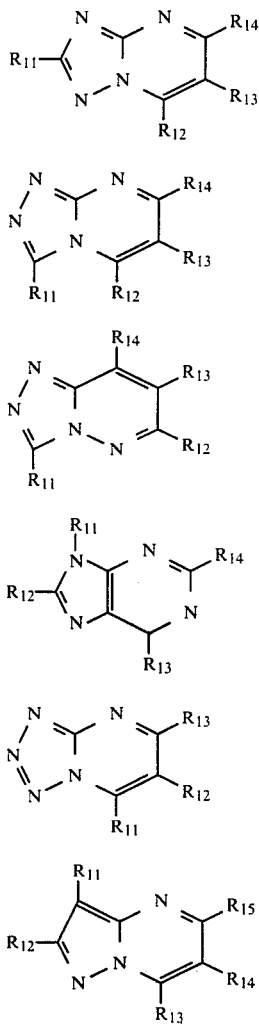

In the foregoing general formulae (IIIa) to (IIIf), substituents $R_{11}$ to $R_{15}$ respectively represent a hydrogen atom, an alkyl group having preferably 1 to 20 carbon atoms, more preferably 1 to 10 carbon atoms, e.g., methyl, ethyl, propyl, octyl, dodecyl, t-butyl, isopropyl, etc. an aryl group having preferably 6 to 20 carbon atoms, more preferably 6 to 10 carbon atoms, e.g., phenyl, naphthyl, etc., an aralkyl group having preferably 7 to 20 carbon atoms, more preferably 7 to 11 carbon atoms, e.g., benzyl, phenylethyl, diphenylmethyl, etc., an amino group, hydroxyl group, an alkoxy group having preferably 1 to 20 carbon atoms, more preferably 1 to 10 carbon atoms, e.g., methoxy, ethoxy, butoxy, isobutoxy, hexyloxy, an alkoxycarbonyl group having preferably 1 to 10 carbon atoms, e.g., ethoxycarbonyl, etc., cyano group or mercapto group; and that, at least one mercapto group must be contained in the compound represented by any general formula described above. In addition, two of the substituents $R_{11}$ to $R_{15}$ may combine with each other and form a ring (e.g., benzene ring, nephthalene ring, cycloalkyl ring or the like).

An alkyl group, an aryl group, an aralkyl group, an amino group, an alkoxy group an so on which are represented by $R_{11}$ to $R_{15}$ may be substituted with a substituent group, such as amino group, a substituted amino group (e.g., diethylamino, etc.), hydroxyl group, an alkoxyl group having preferably 1 to 5 carbon atoms, e.g., methoxy, ethoxy, butoxy, etc., an alkylmercapto group having preferably 1 to 5 carbon atoms, e.g., mercaptomethyl, mercaptopropyl, etc. and so on.

On these mercapto group-containing azaindenes which can be used in the present invention, the tetrazaindenes of the general formulae (IIIa) to (IIId) are more desirable than others.

Now, specific examples of the representatives of the azaindene are illustrated below.

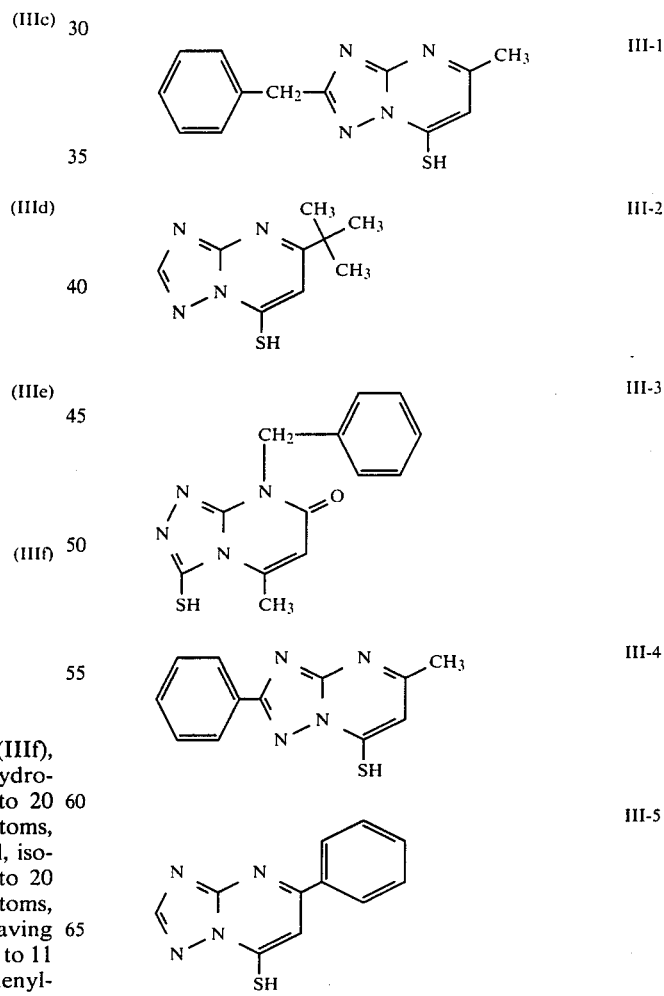

-continued
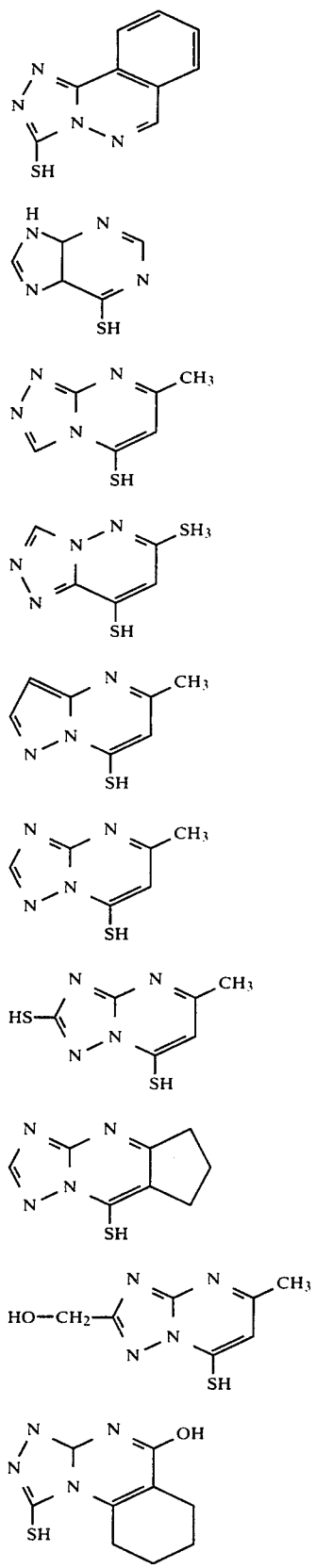
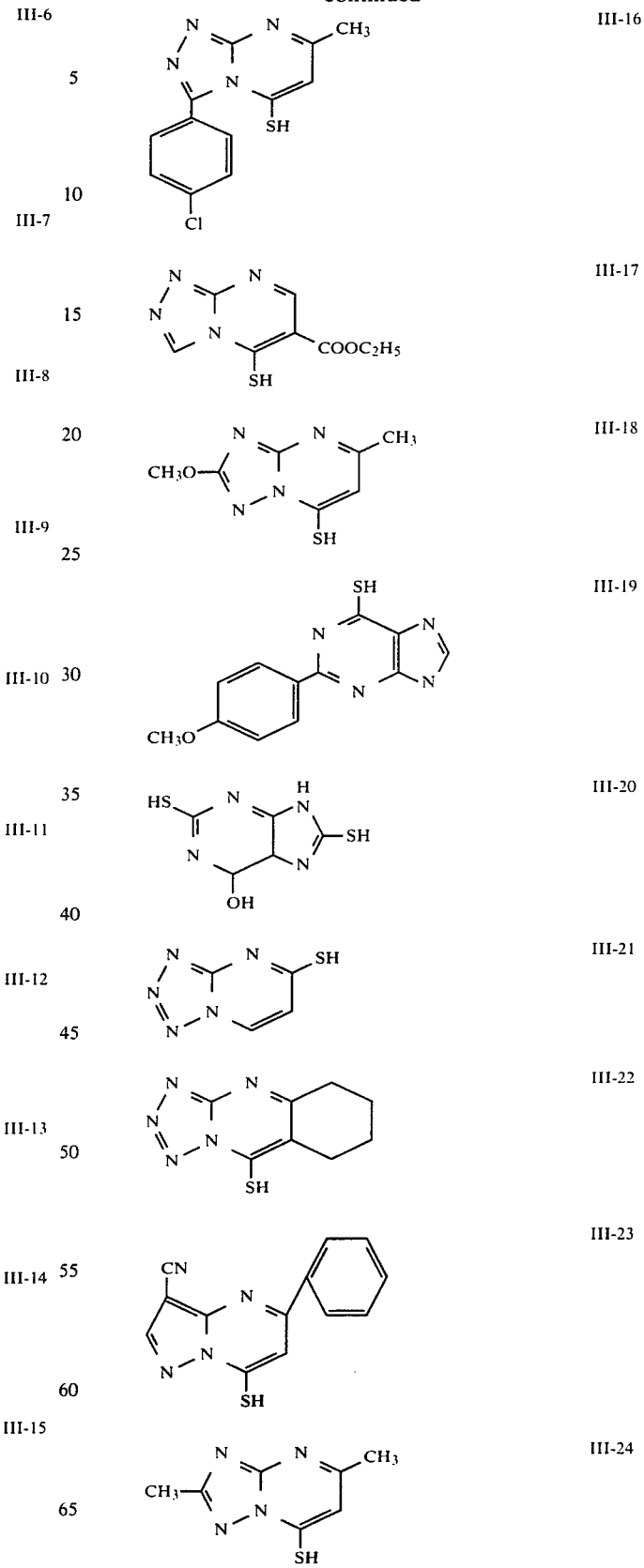

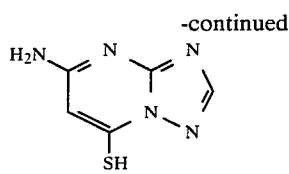

III-25

The mercaptoazaindenes used in the present invention are known compounds, and can be easily prepared from the corresponding hydroxyazaindenes. More specifically, they can be generally obtained by firstly halogenating (e.g., chlorinating) hydroxyazaindenes with a halogenating agent (e.g., phosphorus oxychloride) and then, by converting them into the corresponding thiol compounds using a sulfur compound such as thiourea or the like.

Synthesis examples of the representatives of these azaindenes are illustrated in detail below. Also, the mercaptoazaindene other than those exemplified below can be easily prepared according to the following preparation processes.

Synthesis Example III-1: Synthesis of 4-Mercapto-6-t-butyl-1,3,3a,7-tetrazaindene (Compound III-2)

(1) Synthesis of 4-Chloro-6-t-butyl-1,3,3a,7-tetrazaindene:

A mixture of 20 g of 4-hydroxy-6-t-butyl-1,3,3a,7-tetrazaindene and 80 ml of phosphorus oxychloride was refluxed for 3 to 4 hours at a temperature kept at 140° to 150° C. by means of an oil bath. After excess phosphorus oxychloride was distilled away under reduced pressure, the reaction mixture was poured into ice water. The reaction product was extracted with methylene chloride and dried over anhydrous sodium sulfate. After the removal of methylene chloride by distillation, pale yellow crystals were obtained. Yield 16 g.

(2) Synthesis of 4-Mercapto-6-t-butyl-1,3,3,a,7-tetrazaindene

In 150 ml of ethanol was dissolved 8.7 g of thiourea and thereto, 4-chloro-6-t-butyl-1,3,3a,7-tetrazaindene obtained above was added. The resulting mixture was refluxed for 1.5 hours over a water bath. Thereupon, crystals separated out. After the removal of ethanol by distillation, needle crystals were obtained. These were recrystallized from 1.8 liter each ethanol for twice. Yield 7.4 g, Melting Point 285°–286° C.

A compound having a thiol group on a triazole ring can also be synthesized by the following method.

Synthesis Example III-2: Synthesis of 1,2,4-Triazolo[3,4-a]-phthalazine-3-thiol (Compound III-6)

In pyridine, was dissolved 25 g of 1-hydrazinophthalazine. Thereto, 13 g of carbon disulfide was added dropwise at a temperature of 0° C. The stirring was continued for 30 minutes and then, the temperature of the reaction mixture was raised to 50° C., and the stirring was continued for additional 1 hour. Thereafter, the temperature was lowered to 0° C. again. Upon the addition of excess triethylamine to the resulting solution, hydrogen sulfide gas began to evolve. The temperature of the reaction system was raised and the refluxing was continued for 3 hours. Thereupon, the evolution of the gas ceased, and the reaction system was cooled. Upon cooling, crystals separated out. The crystals were filtered off, and recrystallized from ethanol. Yield 23 g, Melting Point 270°–280° C.

In the present invention, the compounds represented by the general formula (I) or (II) can be used in a combination of two or more thereof. In case of incorporating these compounds in a sensitive material, they may be added to at least one silver halide emulsion layer and a hydrophilic colloidal layer (e.g., a protective layer, an interlayer, etc.) generally in an amount of $1 \times 10^{-5}$ to $1 \times 10^{-1}$ mole, preferably $5 \times 10^{-4}$ to $1 \times 10^{-1}$ mole, per mole of silver halide. When the compound is added in an amount of more than $1 \times 10^{-1}$ mole, the compound tends to dissolve out from the emulsion layer to a processing solution, which results in change of the formation of the solution. The addition may be carried out by dispersing them directly into a silver halide emulsion or a hydrophilic colloid, or by firstly dissolving them in a proper organic solvent such as methanol, ethylene glycol or the like, and then by adding the resulting solution to a silver halide emulsion or a hydrophilic colloid. In the other case of adding them to a processing solution (e.g., developing bath, pre-bath for development), they are preferably employed in an amount of $10^{-5}$ to $10^{-1}$ mole/l, particularly $10^{-4}$ to $10^{-1}$ mole/l.

The mercaptoazaindenes used in the present invention can be used alone or in a combination of two or more thereof. In case of incorporating them in a sensitive material, they can be used within the range of $1 \times 10^{-5}$ to $1 \times 10^{-1}$ mole per 1 mole of internally fogged silver halide grains and preferably, they are added in an amount of $1 \times 10^{-4}$ to $1 \times 10^{-2}$ mole per mole of internally fogged silver halide grains. When it is used in an amount of more than $1 \times 10^{-1}$ mole, the same disadvantages as described for the compounds of general formulae (I) and (II) tend to be encountered. In such a range of the addition amount, the optimum one is in the vicinity (within ±20%) of a saturated adsorption amount on internally fogged grains. The addition may be carried out by dispersing them directly into a hydrophilic colloid, or by adding them in a form of solution in a proper organic solvent, such as methanol, ethylene glycol, etc., to a hydrophilic colloid. The mercaptoazaindenes may be added to a light-sensitive silver halide emulsion or an internally fogged emulsion, both of them, the mixture thereof, a coating composition for forming an interlayer, or a coating composition for forming a protective layer. However, it is more preferable to incorporate them in an internally fogged emulsion in advance. When adding them to a processing solution, they may be incorporated in a developing bath, a pre-bath for development or so on preferably in an amount of from $10^{-5}$ to $10^{-1}$ mole/l, particularly from $10^{-4}$ to $10^{-2}$ mole/l.

It is preferred that the compound represented by the general formulae (I) and (II) and the mercapto group-containing azaindenes, are incorporated in a light-sensitive material.

A desirable time for incorporation of the compound of the general formula (I) or (II) into the sensitive material is after the grain formation of a light-sensitive silver halide emulsion and preferably, the compound is added to the emulsion at the time between the chemical ripening of the emulsion and just before the coating thereof. On the other hand, the azaindenes having a mercapto group are preferably employed at the time between after the grain formation of internally fogged silver halide grains and before the coating thereof. On the occasion that the internally fogged silver halide emulsion is to be mixed with a light-sensitive silver halide emulsion, the mercapto group-containing azaindenes is added preferably before the mixing, and especially the mixing should be carried out after the passage of a time long enough to complete the adsorption of the azaindenes on the grain surfaces of the internally fogged silver halide emulsion.

The expression "light-sensitive" in the present invention means that a sensitivity of the light-sensitive silver halide emulsion is greater than that of the internally fogged silver halide emulsion. More specifically, it means that the light-sensitive silver halide emulsion has a sensitivity 10 times or more, preferably 100 times or more as higher as the sensitivity of the internally fogged silver halide emulsion. The term sensitivity used herein is defined as described below.

Suitable light-sensitive silver halide emulsions which can be used may be any of usual silver halide emulsions, such as a surface latent image type emulsion.

The surface latent image type emulsion is that which, when it is exposed to light for a fixed time between 1/100 to 1 second and developed in accordance with the surface development process (A), as hereinafter defined, has a sensitivity greater than the sensitivity of the same emulsion which has been exposed in the same way and developed in accordance with the internal development process (B), as hereinafter defined, preferably that which exhibits a sensitivity in the former case at least two times as high as that in the latter case. Herein, the sensitivity is defined as follows:

$$S = (100/Eh)$$

wherein S represents a sensitivity, and Eh represents an exposure required for attaining the very middle density between the maximum density ($D_{max}$) and the minimum density ($D_{min}$), i.e., $\frac{1}{2}$ ($D_{max}+D_{min}$).

Surface Development Process (A)

The development is carried out at 20° C. for 10 minutes using a developing solution having the following formula.
N-Methyl-p-aminophenol (Hemisulfate)—2.5 g
Ascorbic Acid—10 g
Sodium Metaborate Tetrahydrate—35 g
Potassium Bromide—1 g
Water to make—1 liter Internal Development Process (B)

The optically exposed emulsion is processed in a bleaching solution containing 3 g/l of a potassium ferricyanide and 0.0126 g/l of phenosafranine at about 20° C. for 10 minutes, washed with water for 10 minutes, and developed at 20° C. for 10 minutes using the developing solution having the following formula:
N-Methyl-p-aminophenol (Hemisulfate)—2.5 g
Ascorbic Acid—10 g
Sodium Metaborate Tetrahydrate—35 g
Potassium Bromide—1 g
Sodium Thiosulfate—3 g
Water to make—1 liter Specific examples of the surface latent image type silver halide include silver chloroiodide, silver iodobromide, silver chloride, silver chlorobromide, silver bromide, and silver chloroiodobromide. Silver bromide and silver iodobromide are preferred. In such silver halides, a desirable iodide content ranges from 0 to 30 mole %, particularly from 0.5 to 10 mole %. A preferable mean grain size of such silver halides is greater than that of a silver halide emulsion having fogging nuclei inside the grains, particularly not less than 0.6 μm. The grain size distribution may be narrow or broad. The silver halide grains in the emulsions may have a regular crystal form, such as that of a cube or an octahedron; an irregular crystal form, such as that of a sphere, a plate or so on; or a composite form thereof. A mixture of various crystal forms of silver halide grains may also be contained. Moreover, silver halide grains having a plate-shaped crystal form in which its diameter is at least 5 times as large as its thickness have an advantageous effect on the present invention.

Photographic emulsions which can be employed in the present invention can be produced in conventional manners as described in P. Glafkides, *Chimie et Physique Photographique*, Paul Montel, Paris (1967); G. F. Duffin, *Photographic Emulsion Chemistry*, The Focal Press, London (1966); V. L. Zelikman et al, *Making and Coating Photographic Emulsion*, The Focal Press, London (1964); and so on. More specifically, they can be produced using the acid process, the neutral process, the ammonia process or any other processes. Suitable methods for reacting a water-soluble silver salt with a water-soluble halide include, e.g., a single jet method, a double jet method and a combination thereof.

Also, a method in which silver halide grains are produced in the presence of excess silver ion (the so-called reversal mixing method) can be employed. Further, the so-called controlled double jet method, in which the pAg of the liquid phase in which silver halide grains are to be precipitated in maintained constant, can also be employed.

According to the above-described method, silver halide emulsions having regular crystal forms and almost uniform grain sizes can be obtained.

Two or more kinds of silver halide emulsions which have been prepared separately may be employed in the form of a mixture.

In a process of producing silver halide grains or allowing the produced silver halide grains to ripen physically, cadmium salt, zinc salts, lead salts, thallium salts, iridium salts or complexes thereof, rhodium salts or complexes thereof, iron salts or complexes thereof and/or the like may be present.

Removal of the soluble salts from the emulsion employed in the present invention is, in general, carried out after the formation of the silver halide grains or after the physical ripening. The removal can be effected using the well-known noodle washing method which comprises gelling the gelatin, or using a sedimentation process (thereby causing flocculation in the emulsion) taking advantage of a polyvalent anion-containing inorganic salt (e.g., sodium sulfate), an anionic surface active agent, an anionic polymer (e.g., polystyrene-sulfonic acid), or a gelatin derivative (e.g., an aliphatic acylated gelatin, an aromatic acylated gelatin, an aromatic carbamoylated gelatin, etc.). The removal of soluble salts from the silver halide emulsion may be omitted.

The silver halide emulsion can be employed in a condition of a so-called un-after-ripened emulsion (e.g., a primitive emulsion), that is to say, a chemically unsensitized emulsion. However, it is usual and preferred for the emulsion to be chemically sensitized. Chemical sensitization can be carried out using processes described in P. Glafkides, supra, V. L. Zelikman et al, supra, or H. Frieser, *Die Grundlagen der Photographischen Prozesse*

*mit Silberhalogeniden,* Akademische Verlagsgesellschaft (1968).

More specifically, sulfur sensitization using compounds containing sulfur capable of reacting with silver ion or active gelatin, reduction sensitization using reducing materials, sensitization with gold or other noble metal compounds, and so on can be employed individually or as a combination thereof. Examples of suitable sulfur sensitizers include thiosulfates, thioureas, thiazoles, rhodanines and other sulfur-containing compounds. Specific examples of such sulfur sensitizers are described in U.S. Pat. Nos. 1,574,944; 2,410,689; 2,278,947; 2,728,668; 3,656,955; 4,032,928 and 4,067,740. Examples of reducing sensitizers include stannous salts, amines, hydrazine derivatives, formamidine sulfinic acid, silane compounds and so on, and specific examples of these sensitizers are described in U.S. Pat. Nos. 2,487,850; 2,419,974; 2,518,698; 2,983,609; 2,983,610; 2,694,637; 3,930,867 and 4,054,458. Group VIII metal complexes such as those of platinum, iridium, palladium, etc., other than gold metal complexes, can be employed for the purpose of sensitization with a noble metal, and specific examples of these metal complexes are described in U.S. Pat. Nos. 2,399,083 and 2,448,060; British Pat. No. 618,061; and so on.

In the photographic light-sensitive material used in the present invention, various kinds of hydrophilic colloids can be employed as a binder.

Suitable colloids which can be used for the above-described purpose include hydrophilic colloids which have generally been employed in the photographic art, such as gelatin, colloidal albumine, polysaccharides, cellulose derivatives and synthetic resins (e.g., polyvinyl compounds including polyvinyl alcohol, acrylamide polymers, etc.). In addition to a hydrophilic colloid, such as a dispersion of a polymerized vinyl compound, especially one which can contribute to enhancement of the dimensional stability of the photographic material, can be incorporatd in a binder composition. Suitable compounds of such a kind include water-insoluble polymers prepared by polymerizing a vinyl monomer such as an alkylacrylate or alkylmethacrylate, acrylic acid, a sulfoalkylarylate or sulfoalkylmethacrylate, etc.

The above-described photographic emulsion can contain a wide variety of compounds for purposes of preventing the lowering of the sensitivity and generation of fog during production, storage or processing of the sensitive material. A great number of compounds have been known to function as those which answer the above-described purposes, and suitable examples thereof include various heterocyclic compounds including 4-hydroxy-6-methyl-1,3,3a,7-tetrazaindene, 3-methyl-benzothiazole, 1-phenyl-5-mercaptotetrazole, etc.; mercury-containing compounds; mercapto compounds; metal salts; and so on.

Specific examples of the compounds which can be employed are described in not only C. E. K. Mees, *The Theory of the Photographic Process,* 3rd Ed. (1966) along with their respective cited references, but also U.S. Pat. Nos. 1,758,576; 2,110,178; 2,131,038; 2,173,628; 2,697,040; 2,304,962; 2,324,123; 2,394,198; 2,444,605; 2,444,606; 2,444,607; 2,444,608; 2,566,245; 2,694,716; 2,697,099; 2,708,162; 2,728,663; 2,728,664; 2,728,665; 2,476,536; 2,824,001; 2,843,491; 2,886,437; 3,052,544; 3,137,577; 3,220,839; 3,226,231; 3,236,652; 3,251,691; 3,252,799; 3,287,135; 3,326,681; 3,420,668 and 3,662,339; British Pat. Nos. 893,428; 403,789; 1,173,609 and 1,200,188; and so on.

The silver halide emulsions having fog nuclei inside the grains which can be used in the sensitive material of the present invention are those which, when examined a piece obtained by coating the emulsion on a transparent support at a coverage of, e.g., 2 g/m² based on silver, by developing at 35° C. for 2 minuits using D-19 (developing solution designated by Eastman Kodak Company) without exposing to light, have a transmission fog density of 0.5 or below (exclusive of the density of the support per se) and that, when examined by developing an identical test piece at 35° C. for 2 minutes using a developing solution prepared by adding 0.5 g/l of potassium iodide to D-19 without exposing to light, have a trasnmission fog density of 1.0 or above (exclusive of the density of the support per se).

The silver halide emulsions having fog nuclei inside the grains can be prepared using various known techniques. Suitable fogging techniques include irradiation with light or X-ray, a technique of forming fog nuclei chemically using a reducing agent, a gold compound or a sulfur-containing compound, a technique of preparing an emulsion under the condition of low pAg and high pH, and so on. In order to produce fog nuclei only inside the grains, although the process which comprises fogging both the interior and surface of silver halide grains using the above-described technique and bleaching fog nuclei present at the grain surface with a potassium ferricyanide solution or the like may be employed, it is more advantageous to employ the process that a core emulsion having fog nuclei is firstly prepared using the technique of carrying out the preparation under the condition of low pAg and high pH, or a chemically fogging method and then, silver halide grains in the core emulsion are covered with a silver halide of a shell emulsion. Preparation methods of this core-shell emulsion are well-known, and for carrying out the preparation thereof descriptions in, e.g., U.S. Pat. No. 3,206,313 can be referred to.

Control of the depth of the internal fog nuclei from the grain surface can be effected with ease by changing the conditions (e.g., a processing time, a temperature and a concentration of a processing solution to be used, etc.) under which fog nuclei present at individual grain surfaces are bleached using, e.g., a potassium ferricydnide solution. On the other hand, in case of a core-shell emulsion also, internal fog nuclei can be easily located at a desired depth by controlling the addition amount (i.e., thickness) of the shell emulsion.

In the internally fogged grains, fog nuclei are preferably located at a depth of not less than $0.2\mu$ on the average, more preferably more than $0.04\mu$, from the grain surface. It is preferable that fog nuclei is located at such a depth that the sensitive material may not generate uneven stains when processed with a fixing solution immediately after the development step without passing through a stop bath.

A silver halide emulsion having fog nuclei inside the grains which can be employed has a mean grain size smaller than that of a surface latent image type silver halide emulsion to be used in combination, and it is suitable for obtaining a high covering power and a desired tone that the mean grain size of the internally fogged emulsion ranges from 1.0 to 0.05 $\mu$m, preferably from 0.6 to 0.1 $\mu$m, and more preferably from 0.5 to 0.1 $\mu$m.

The term grain size of silver halide in the present invention refers to the diameter of grains when they have a spherical or nearly spherical shape, and the diameter of spheres having the same volume as the grains have when they have another shape (e.g., cube, plate, etc.).

Suitable silver halides which constitute internally fogged emulsions can be any conventional ones, e.g., silver bromide, silver iodobromide, silver iodochlorobromide, silver chlorobromide, silver chloride, etc.

The ratio of the content of a light-sensitive silver halide to the content of an intenally fogged silver halide in the silver halide photographic material used in the present invention can be changed depending upon types of emulsions used (e.g., halide composition), the kind or the end-use purpose of a sensitive material to be produced and specifically ranges from 100:1 to 1:100 (by weight), particularly from 10:1 to 1:10. A preferable coverage of silver is 0.5 to 10 g/m$^2$ in total.

As for the structure of constituent layers of the photographic material according to the present invention, some embodiments can be thought out. Representative embodiments of the layer structure are described below. (1) An embodiment in which all of four essential constituents, namely light-sensitive silver halide grains, internally fogged silver halide grains, at least one compound represented by the general formulae (I) or (II) and mercaptoazaidene, are incorporated in the same coating composition (emulsion) and coated on a support and thereon, a protective layer may be further provided; (2) an embodiment in which an emulsion containing three constituents, namely internally fogged silver halide grains, at least one compound represented by the general formula (I) or (II) and mercaptoazaindene, is firstly coated on a support, and thereon is coated a light-sensitive silver halide emulsion, and further a protective layer may be provided on the resulting emulsion layer; (3) an embodiment in which an emulsion containing three constituents, namely internally fogged silver halide grains, at least one compound represented by general formula (I) or (II) and mercaptoazaindenes, is firstly coated on a support, and then an emulsion containing light-sensitive silver halide grains and at least one compound represented by the general formula (I) or (II) is coated thereon, and further a protective layer may be provided on the resulting emulsion layer; (4) an embodiment in which an emulsion containing both internally fogged silver halide grains and light-sensitive silver halide grains is coated on a support, and thereon a protective layer containing at least one compound represented by the general formula (I) or (II) and mercaptoazaindenes is provided; (5) an embodiment in which an emulsion layer containing four constituents, namely light-sensitive silver halide grains, internally fogged silver halide grains, at least one compound represented by the general formula (I) or (II) and mercaptoazaindenes is firstly provided on a support and then, an emulsion containing light-sensitive silver halide grains and at least one compound represented by the general formulae (I) or (II) is coated thereon, and further protective layer may be provided on the resulting emulsion layer; (6) an embodiment in which an emulsion layer containing all of four constituents, namely light-sensitive silver halide grains, internally fogged silver halide grains, at least one compound represented by the general formula (I) or (II) and mercaptoazaindenes, is firstly provided on a support, and thereon is coated an emulsion containing the same four constituents as in the lower layer with a composition different from that of the lower layer, and further thereon may be provided a protective layer; (7) an embodiment in which a layer structure according to the embodiments (1) to (6), or a layer structure which accords with the embodiments (1) to (6) except that the compound represented by the general formula (I) or (II) is removed therefrom is employed, and a developing solution to be used in association with the sensitive material having this layer structure contains at least one compound represented by the formula (I) or (II); (8) an embodiment in which a layer structure which accords with the embodiments (1) to (6), or a layer structure which accords with the embodiments (1) to (6) except that mercaptoazaindenes are removed therefrom is employed, and mercaptoazaindenes are added to a developing solution to be used in association with the sensitive material having such a layer structure; (9) an embodiment in which a layer structure which accords with the embodiments (1) to (6), or a layer structure which accords with the embodiments (1) to (6) except that both the compound represented by the general formula (I) or (II) and mercaptoazaindenes are removed therefrom is employed and that, a developing solution containing both at least one compound represented by the general formula (I) or (II) and mercaptoazaindenes is used in association with the sensitive material having such a layer structure; and so on can be realized.

In addition, each layer structure described above may be provided on not only one side of a support but also both sides thereof.

The protective layer of the silver halide photographic material of the present invention comprises a hydrophilic colloid, and suitable examples of hydrophilic colloids which can be used include those described hereinbefore. In addition, the protective layer may be either single or double.

The silver halide photographic material of the present invention may contain a matting agent and/or a smoothing agent in its emulsion layer(s) or its protective layer, especially its protective layer. Suitable examples of the matting agent include organic compounds such as water dispersible vinyl polymers, e.g., polymethylmethacrylate particles having a proper size (ranging from 0.3 to 5μ, or preferably at least two times, more preferably at least 4 times as greater as the thickness of the protective layer) and inorganic compounds such as silver halides, strontium barium sulfate, etc. The smoothing agent is not only useful for the prevention of adhesion troubles, in analogy with the matting agent, but also especially effective for improvement on abrasion charcteristics which affect the camera adaptation at the time of photographing or porjection using motion picture films. Specific examples of the smoothing agent which can be used include liquid paraffin; waxes such as higher fatty acid esters; polyfluorinated hydrocarbons and the derivatives thereof; silicones such as polyalkylpolysiloxanes, polyarylpolysiloxanes, polyalkylarylpolysiloxanes and polyalkylene oxide adducts thereof; and so on.

The silver halide photographic material of the present invention can additionally have an antihalation layer, an interlayer, a filter layer and so on, if necessary.

In the sensitive material of the present invention, photographic silver halide emulsion layers and other hydrophilic colloid layers can be hardened with any proper hardeners. Examples of these hardeners include vinyl sulfonyl compounds active halogen-containing hardeners; dioxane derivatives; oxypolysaccharides like oxystarch; and so on as described in published unexamined Japanese Patent Application Nos. 76025/78, 76026/78 and 77619/78.

The photographic silver halide emulsion layers can further contain other additives, especially photographically useful agents such as a lubricant, a sensitizer, a light absorbing agent, a plasticizer and so on.

Further, the silver halide emulsion of the present invention can contain an iodine ion-releasing compound (e.g., potassium iodide), and furthermore a desired image can be obtained by using a developing solution containing iodine ion.

The sensitive material of the present invention can contain in its hydrophilic colloidal layers a water soluble dye as a filter dye, or for other purposes such as antiirradiation, antihalation and so on. Examples of such a dye include oxonol dyes, hemioxonol dyes, styryl dyes, merocyanine dyes, cyanine dyes and azo dyes. Of these dyes, oxonol dyes, hemioxonol dyes and merocyanine dyes are more useful for the above-described purposes.

In the sensitive material of the present invention, the hydrophilic colloidal layer containing a dye or an ultraviolet absorbent may be mordanted by cationic polymers.

The sensitive material of the present invention may contain surface active agents for various purposes. Any kinds of surface active agents, nonionic, ionic or amphoteric ones, can be employed, and proper ones are selected therefrom depending upon the purpose. Specific examples of the surface active agents which can be used include polyoxyalkylene derivatives, amphoteric amino acids (including sulfobetaines) and so on. These surface active agents are described in U.S. Pat. Nos. 2,600,831; 2,271,622; 2,271,623; 2,275,727; 2,787,604; 2,816,920 and 2,739,891; and Belgian Pat. No. 652,862.

In the sensitive material of the present invention, its photographic emulsions may be spectrally sensitized in a blue light region having relatively longer wavelengths, a green light region, a red light region, or an infrared region. Suitable examples of sensitizing dyes which can be used include cyanine dyes, merocyanine dyes, complex cyanine dyes, complex merocyanine dyes, holopolar cyanine dyes, styryl dyes, hemicyanine dyes, oxonol dyes, hemioxonol dyes and so on.

Useful sensitizing dyes which can be used in the present invention are described in U.S. Pat. Nos. 3,522,052; 3,619,197; 3,713,828; 3,615,643; 3,615,632; 3,617,293; 3,628,964; 3,703,377; 3,666,480; 3,667,960; 3,679,428; 3,672,897; 3,769,026; 3,556,800; 3,615,613; 3,615,638; 3,615,635; 3,705,809; 3,632,349; 3,677,765; 3,770,449; 3,770,440; 3,769,025; 3,745,014; 3,713,828; 3,567,458; 3,625,698; 2,526,632; and 2,503,776; published unexamined Japanese Patent Application No. 76525/73; Belgian Pat. No. 691,807; and so on.

In the present invention, a sensitizing dye can be employed in an amount equivalent to one which used in a conventional negative silver halide emulsion. In particular, it is advantageous to use the sensitizing dye in such an amount as not to lower substantially the inherent sensitivity of the silver halide emulsion. More specifically, it is desirable to use the sensitizing dye in an amount of about $1.0 \times 10^{-5}$ to about $5 \times 10^{-4}$ mole, particularly about $4 \times 10^{-5}$ to $2 \times 10^{-4}$ mole, per mole of light-sensitive silver halide.

Photographic emulsion layers and other layers are provided on one side or both sides of a flexible support which has been conventionally used in photographic materials, resulting in the formation of a sensitive material of the present invention. Suitable materials which are available for the flexible support include films of cellulose acetate, cellulose acetate butyrate, polystyrene, polyethylene terephthalate and other synthetic polymers, and sheets of paper coated or laminated with baryta, $\alpha$-olefin polymers (e.g., polyethylene, polypropylene, ethylene/butylene copolymer, etc.) and so on.

In producing the photographic material of the present invention, the photographic emulsion layers and other hydrophilic colloidal layers are provided on a support or other layers using various known techniques. Specifically, the coating can be carried out using a dip coating technique, a roller coating technique, a curtain coating technique, an extrusion coating technique or the like.

The present invention can be applied to all kinds of photographic materials, provided that they require high sensitivity or high contrast. For instance, the present invention can be applied to X-ray photographic materials, lithographic photosensitive materials, black and white negative pHotographic materials, color negative photosensitive materials, color paper photosensitive materials and so on.

In addition, the present invention can be applied to diffusion transfer photographic materials, color diffusion transfer photographic materials and the like in which a positive image is produced by dissolving undeveloped silver halide and making it be deposited on an image receiving layer close to the silver halide emulsion layer.

The photographic processing of the sensitive material of the present invention can be effected using known methods and processing solutions, such as those described in, e.g., Research Disclosure, vol. 176, pp. 28–30 (RD-17643). This photographic processing may be either a photographic processing for forming a silver image (black and white photographic processing) or a photographic processing for forming a color image (color photographic processing) according to the end-use purpose of the sensitive material to be processed. The processing temperature is usually selected from the range of 18° C. to 50° C. Of course, processing temperatures lower than 18° C. or those higher than 50° C. may be employed as occasion calls.

A developing solution for a black and white photographic processing can contain a known developing agent. As the developing agent, hydroxybenzenes (e.g., hydroquinone), 3-pyrazolidones (e.g., 1-phenyl-3-pyrazolidone), aminophenols (e.g., N-methyl-p-aminophenol) and the like can be employed individually or in a combination of two or more thereof. In addition, the light sensitive material of the present invention can also be processed with a developing solution containing imidazoles as the silver halide solvent described in published unexamined Japanese Patent application No. 78535/57. Further, the sensitive material of the present invention can also be processed with a developing solution containing both such a silver halide solvent and an additive like an indazole or a triazole as described in published unexamined Japanese Patent application No. 37643/83. In addition to the above-described ingredients, the developing solution may generally contain a known preservative, a known alkali agent, a known pH buffer agent, a known antifoggant, and so on. Further, a dissolution aid, a color toning agent, a development accelerator, a surface active agent, a defoaming agent, a water softener, a hardener, a viscosity imparting agent and so on may be optionally added to the developing solution.

Furthermore, a so-called "lithographic" development processing can be applied to the photographic emulsions of the present invention. The term "lithographic" development processing refers to the development processing made to proceed infectiously using a developing solution which contains a dihydroxybenzene as a developing agent and a small amount of sulfite ion in order to reproduce line image photographically, or to effect photographic reproduction of halftone image by dots (details thereof are described in L. F. A. Mason, Photographic Processing Chemistry, pp. 163–165, Focal Press, London (1966)).

On the other hand, a special method in which a developing agent is incorporated in a photographic material, especially in its emulsion layer, and the resultant photographic material is processed with an aqueous alkaline solution to achieve development may be employed. Among many usable developing agents, hydrophobic ones can be incorporated in emulsion layers using various methods as described in, e.g., Research Disclosure, vol. 169 (RD-16928); U.S. Pat. No. 2,739,890; British Pat. No. 813,253; West German Pat. No. 1,547,763; or so on. Such a development-processing as described above may be carried out in combination with a silver salt stabilizing treatment using a thiocyanate.

As for the fixing solution, those having conventionally used compositions can also be employed for the sensitive material of the present invention. Usable fixing agents include not only thiosulfates and thiocyanates, but also organic sulfur compounds which have been known to have a fixing effect. Fixing solutions may contain water-soluble aluminium salts as a hardener.

The present invention will now be illustrated in more detail by reference to the following examples.

EXAMPLE 1

(1) Preparation of Light-Sensitive Silver Halide Emulsion

According to a conventional ammonia process, a silver iodobromide emulsion having a mean grain size of $1.3\mu$ (AgI: 2 mol.%) was prepared from silver nitrate, potassium bromide and potassium iodide. The emulsion prepared was subjected to chemical sensitization consisting of gold-sulfur sensitization using chloroauric acid and sodium thiosulfate. After removal of salts using an usual coagulation method, 4-hydroxy-6-methyl-1,3,3a,7-tetrazaindene was added to the emulsion as a stabilizing agent. Thus, the light-sensitive silver iodobromide emulsion A was obtained.

(2) Preparation of Internally Fogged Emulsion

An aqueous solution of silver nitrate and an aqueous solution of potassium bromide were added simultaneously to a 2 wt% aqueous solution of gelatin maintained at 55° C. with stirring to produce core grains having a mean grain size of $0.29\mu$. A temperature of the resultant emulsion was raised to 75° C. and thereto, sodium hydroxide and silver nitrate were added in proper amounts to carry out the ripening for a period of 15 minutes. Thus, fog nuclei were formed at the individual surfaces of core grains. The temperature was lowered to 55° C., and pH and pAg were returned to their original values by adding acetic acid and potassium bromide to the emulsion. Thereto, a silver nitrate aqueous solution and a potassium bromide aqueous solution were further added simultaneously. The resulting emulsion was desalted using the usual coagulation method and then, dispersed again into a gelatin aqueous solution. Thus, the internally fogged silver bromide emulsion B having a mean grain size of $0.37\mu$ was obtained.

(3) Preparation of Comparative Samples 1 to 5

An emulsion obtained by mixing the light-sensitive silver halide emulsion A prepared in the above-described manner (1) with the internally fogged emulsion B prepared in the above-described manner (2), and a gelatin aqueous solution for forming a protective layer were uniformly coated in this order on a polyester base provided with a subbing layer to produce the comparative sample 1. Next, the compounds III-1 and III-7, which are illustrated as mercaptoazaindenes hereinbefore, were added in advance to separate portions of the internally fogged emulsion B at the rate of $1.7 \times 10^{-3}$ mole per mole of silver halide in emulsion B. Then, each of these emulsions was mixed with the light-sensitive silver halide emulsion A. Each of the resultant emulsions and a gelatin aqueous solution for foming a protective layer were uniformly coated in this order on the same base as described above. Thus, the comparative samples 2 and 3 were obtained. In addition, the compound I-12, which is illustrated as the compound represented by the general formula (I), and the compound II-3, which is illustrated as the compound represented by the general formula (II), were added to separate portions of the emulsion prepared by mixing the light-sensitive silver halide emulsion A with the internally fogged emulsion B at the rate of $1 \times 10^{-2}$ mole per mole of silver halide of the mixed emulsion. Subsequently, each of the resultant emulsions and a gelatin aqueous solution for forming a protective layer were uniformly coated in this order on the same base as described above. Thus, the comparative samples 4 and 5 were obtained.

In all of the comparative samples 1 to 5, the coverages of the emulsion A and that of the emulsion B were adjusted to 1.7 g/m² reduced to silver basis, the protective layer was adjusted so as to contain 1.3 g/m² of gelatin, and all of emulsion layers were adjusted so as to contain 2.2 g/m² of gelatin.

(4) Preparation of Samples 6 to 13 of the Present Invention

The illustrated compound III-1 was added in advance to the internally fogged emulsion B prepared in the above-described manner (2) at the rate of $1.7 \times 10^{-3}$ mole per mole of silver halide, and the resulting emulsion was divided into seven portions. With each portion of the emulsion, the light-sensitive silver halide emulsion A prepared in the above-described manner (1) was admixed. To the resultant four portions out of seven, the illustrated compounds I-11, I-12, I-13 and II-3 were added separately at the rate of $1 \times 10^{-2}$ mole per mole of silver halide of the mixed emulsion. On the other hand, to the residual three portions were added the illustrated compounds I-14, I-15 and I-16 separately at the rate of $2.5 \times 10^{-3}$ mole per mole of silver halide of the mixed emulsion. Subsequently, each of the resultant emulsions and a gelatin aqueous solution for forming a protective layer were uniformly coated in this order on a polyester base provided with a subbing layer. Thus, samples 6 to 12 of the present invention were obtained. Further, the illustrated compound III-7 was added in advance to the internally fogged emulsion B at the rate of $1.7 \times 10^{-3}$ mole per mole of silver halide, and the resulting emulsion was mixed with the light-sensitive silver halide emulsion A. Thereto, the illustrated compound I-12 was added at the rate of $1 \times 10^{-2}$ mole per mole of the silver halide in the mixed emulsion. Next, the resultant emulsion and a gelatin aqueous solution for forming a protective layer were uniformly coated in this order on the same base as described above. Thus, sample 13 of the present invention was obtained.

In all of the samples 6 to 13, the coverages of the emulsion A and that of the emulsion B were adjusted equally to 1.7 g/m² reduced to silver basis, the protective layer was adjusted so as to contain 1.3 g/m² of gelatin, and all of the emulsion layers were adjusted so as to contain 2.2 g/m² of gelatin.

(5) Test pieces of the comparative samples 1 to 5 and samples 6 to 13 of the present invention respectively were wedgewise exposed to light, developed at 35° C. for 25 seconds using a developing solution having the following formula and then, subjected, to, in sequence, stop, fixation, washing and drying processings. The thus processed test pieces were submitted to sensitometry.

(Developing Solution A)

Potassium Hydroxide—29.14 g
Glacial Acetic Acid—10.06 g
Potassium Sulfite—44.20 g
Sodium Hydrogencarbonate—7.50 g
Boric Acid—1.00 g
Diethylene Glycol—28.96 g
Ethylenediaminetetraacetic Acid—1.67 g
5-Methylbenzotriazole—0.06 g
5-Nitroindazole—0.25 g
Hydroquinone—30.00 g
1-Phenyl-3-pyrazolidone—1.50 g
Glutaraldehyde—4.93 g
Sodium Metahydrogensulfite—12.60 g
Potassium Bromide—3.70 g
Water to make—1 liter
pH adjusted to—10.25

Results obtained are set forth in Table 1.

TABLE 1

| Remark | Sample No. | Compound of general formula (I) or (II) (addn. amt. per mol. of silver halide) | Mercaptoazaindenes (addn. amt. per mol. of silver halide of emulsion B) | Photographic Properties | | | |
|---|---|---|---|---|---|---|---|
| | | | | Relative Sensitivity | Maximum Density | Gamma | Fog Value |
| Comparison | 1 | Not added | Not added | 100 | 0.8 | 0.4 | 0.05 |
| " | 2 | " | III-1 ($1.7 \times 10^{-3}$ mol.) | 80 | 1.7 | 0.4 | 0.02 |
| " | 3 | " | III-7 ($1.7 \times 10^{-3}$ mol.) | 85 | 1.7 | 0.5 | 0.03 |
| " | 4 | I-12 ($1 \times 10^{-2}$ mol.) | Not added | 100 | 0.8 | 0.4 | 0.05 |
| " | 5 | II-3 ($1 \times 10^{-2}$ mol.) | " | 95 | 0.8 | 0.4 | 0.07 |
| Present Invention | 6 | I-11 ($1 \times 10^{-2}$ mol.) | III-1 ($1.7 \times 10^{-3}$ mol.) | 300 | 2.8 | 4.0 | 0.04 |
| Present Invention | 7 | I-12 ($1 \times 10^{-2}$ mol.) | III-1 ($1.7 \times 10^{-3}$ mol.) | 250 | 2.8 | 3.3 | 0.02 |
| Present Invention | 8 | I-13 ($1 \times 10^{-2}$ mol.) | III-1 ($1.7 \times 10^{-3}$ mol.) | 200 | 2.8 | 1.3 | 0.03 |
| Present Invention | 9 | I-14 ($2.5 \times 10^{-3}$ mol.) | III-1 ($1.7 \times 10^{-3}$ mol.) | 220 | 2.8 | 1.6 | 0.02 |
| Present Invention | 10 | I-15 ($2.5 \times 10^{-3}$ mol.) | III-1 ($1.7 \times 10^{-3}$ mol.) | 230 | 2.8 | 3.3 | 0.05 |
| Present Invention | 11 | I-16 ($2.5 \times 10^{-3}$ mol.) | III-1 ($1.7 \times 10^{-3}$ mol.) | 250 | 2.8 | 3.2 | 0.04 |
| Present Invention | 12 | II-3 ($1 \times 10^{-2}$ mol.) | III-1 ($1.7 \times 10^{-3}$ mol.) | 110 | 2.0 | 0.7 | 0.04 |
| Present Invention | 13 | I-12 ($1 \times 10^{-2}$ mol.) | III-7 ($1.7 \times 10^{-3}$ mol.) | 280 | 2.8 | 3.5 | 0.02 |

(Herein, sensitivities are expressed taking the sensitivity of Sample No. 1 as 100)

As can be seen from Table 1, the comparative sample 1 and the comparative samples 2 to 5 in each of which a mercaptoazaindene or the compound of the general formula (I) or (II) was contained independently were unable to exhibit sufficiently high sensitivity, maximum density and gamma value when developed with a developing solution having a bromine ion concentration almost equal to half those of conventional developing solution.

On the other hand, the samples 6 to 13 of the present invention, which contained both compounds of the present invention, i.e., a mercaptoazaindene and the compound represented by the general formula (I) or (II), had high sensitivities, high contrast and high maximum densities, that is to say, they exhibited the intended effects to the full. Namely, the combined use of the mercaptoazaindene and the compound represented by the general formula (I) or (II) has made possible the production of images having high contrast and high maximum density with a high photographic speed even when development is carried out under a low bromine ion concentration.

EXAMPLE 2

A test piece of the comparative sample 1 and those of the present invention samples 6 to 13 were wedgewise exposed to light and then, each of them was developed at 35° C. for 25 seconds using Developing Solution B which had the same composition as Developing Solution A used in Example 1 except that a content of KBr was changed to 7.00 g, followed by stop, fixation, washing and drying treatments. The thus processed test pieces were subjected to sensitometry. Results obtained are shown in Table 2.

TABLE 2

| Remark | Sample No. | Compound of general formula (I) or (II) (addn. amt. per mol. of silver halide) | Mercaptoazaindenes (addn. amt. per mol. of silver halide in emulsion B) | Photographic Properties | | | |
|---|---|---|---|---|---|---|---|
| | | | | Relative Sensitivity | Maximum Density | Gamma | Fog Value |
| Comparison | 1 | Not added | Not added | 100 | 0.8 | 0.4 | 0.06 |
| Present Invention | 6 | I-11 ($1 \times 10^{-2}$ mol.) | III-1 ($1.7 \times 10^{-3}$ mol.) | 310 | 2.8 | 3.5 | 0.04 |
| Present Invention | 7 | I-12 ($1 \times 10^{-2}$ mol.) | III-1 ($1.7 \times 10^{-3}$ mol.) | 260 | 2.8 | 3.3 | 0.02 |
| Present Invention | 8 | I-13 ($1 \times 10^{-2}$ mol.) | III-1 ($1.7 \times 10^{-3}$ mol.) | 210 | 2.8 | 1.5 | 0.03 |
| Present Invention | 9 | I-14 ($2.5 \times 10^{-3}$ mol.) | III-1 ($1.7 \times 10^{-3}$ mol.) | 300 | 2.8 | 3.4 | 0.02 |
| Present Invention | 10 | I-15 ($2.5 \times 10^{-3}$ mol.) | III-1 ($1.7 \times 10^{-3}$ mol.) | 250 | 2.8 | 3.5 | 0.05 |
| Present Invention | 11 | I-16 ($2.5 \times 10^{-3}$ mol.) | III-1 ($1.7 \times 10^{-3}$ mol.) | 280 | 2.8 | 3.5 | 0.04 |
| Present Invention | 12 | II-3 ($1 \times 10^{-2}$ mol.) | III-1 ($1.7 \times 10^{-3}$ mol.) | 170 | 2.5 | 0.9 | 0.04 |
| Present Invention | 13 | I-12 ($1 \times 10^{-2}$ mol.) | III-7 ($1.7 \times 10^{-3}$ mol.) | 290 | 2.8 | 3.5 | 0.02 |

(Herein, sensitivities are expressed taking the sensitivity of Sample No. 1 as 100)

As can be seen from Table 2, in analogy with the results of Example 1 which was obtained by using Developing Solution A having a low bromine ion concentration, the samples 6 to 13 can also provide images of high sensitivities, high contrasts and high maximum densities by the development using Developing Solution B having a typical bromine ion concentration.

EXAMPLE 3

A test piece of the comparative sample 1 and those of the samples 6 to 13 of the present invention were wedgewise exposed to light and then, developed using Developing Solution C having the following formula at 20° C. for 4 minutes, and thereafter subjected to, in sequence, stop, fixation, washing and drying processings. The thus processed test pieces were subjected to sensitometry.

(Developing Solution C)

1-Phenyl-3-pyazolidone—0.5 g
Hydroquinone—20.0 g
Disodium Ethylenediaminetetraacetate—2.0 g
Potassium Sulfite—60.0 g
Boric Acid—4.0 g
Potassium Carbonate—20.0 g
Sodium Bromide—20.0 g
Diethylene Glycol—30.0 g
Water to make—1 liter
NaOH to adjust pH to 10.0
Results obtained are shown in Table 3.

TABLE 3

| Remark | Sample No. | Compound of general formula (I) or (II) (addn. amt. per mol. of silver halide) | Mercaptoazaindenes (addn. amt. per mol. of silver halide in emulsion B) | Photographic Properties | | | |
|---|---|---|---|---|---|---|---|
| | | | | Relative Sensitivity | Maximum Density | Gamma | Fog Value |
| Comparison | 1 | Not added | Not Added | 100 | 0.7 | 0.4 | 0.05 |
| Present Invention | 6 | I-11 ($1 \times 10^{-2}$ mol.) | III-1 ($1.7 \times 10^{-3}$ mol.) | 400 | 2.8 | 4.5 | 0.02 |
| Present Invention | 7 | I-12 ($1 \times 10^{-2}$ mol.) | III-1 ($1.7 \times 10^{-3}$ mol.) | 350 | 2.8 | 6.0 | 0.01 |
| Present Invention | 8 | I-13 ($1 \times 10^{-2}$ mol.) | III-1 ($1.7 \times 10^{-3}$ mol.) | 300 | 2.8 | 6.0 | 0.02 |
| Present Invention | 9 | I-14 ($2.5 \times 10^{-3}$ mol.) | III-1 ($1.7 \times 10^{-3}$ mol.) | 320 | 2.8 | 6.0 | 0.03 |
| Present Invention | 10 | I-15 ($2.5 \times 10^{-3}$ mol.) | III-1 ($1.7 \times 10^{-3}$ mol.) | 330 | 2.8 | 6.5 | 0.06 |
| Present Invention | 11 | I-16 ($2.5 \times 10^{-3}$ mol.) | III-1 ($1.7 \times 10^{-3}$ mol.) | 350 | 2.8 | 6.4 | 0.05 |
| Present Invention | 12 | II-3 ($1 \times 10^{-2}$ mol.) | III-1 ($1.7 \times 10^{-3}$ mol.) | 200 | 2.5 | 1.7 | 0.04 |
| Present Invention | 13 | I-12 ($1 \times 10^{-2}$ mol.) | III-7 ($1.7 \times 10^{-3}$ mol.) | 380 | 2.8 | 6.5 | 0.03 |

(Sensitivities set forth in the table are expressed taking the sensitivity of sample No. 1 as 100)

As can be seen from Table 3, the samples 6 to 13 of the present invention can also provide images of high sensitivities, high contrasts and high maximum densities by usual low temperature development.

EXAMPLE 4

(1) Preparation of Sample 14 of the Present Invention

To the internally fogged emulsion B prepared in the manner (2) described in Example 1, the illustrated compound III-1 was added in advance in an amount of $1.7 \times 10^{-3}$ mole per 1 mole of silver halide and thereto, the illustrated compound I-12 was further added in an amount of $2 \times 10^{-2}$ mole per 1 mole of silver halide. Subsequently, the resultant emulsion, the light-sensitive silver halide emulsion A alone which has been prepared in the manner (1) of Example 1, and a gelatin aqueous solution for forming a protective layer were coated in this order in uniform layers on a polyester base provided with a subbing layer. Thus, the sample 14 of the present invention in which silver halide emulsions were coated in a double layer was obtained.

Therein, the silver coverage of the emulsion B in the lower emulsion layer was adjusted to 1.7 g/m², the silver coverage of the emulsion A in the upper emulsion layer was adjusted to 1.7 g/m², and the protective layer was adjusted so as to contain 1.3 g/m² of gelatin and the emulsion layers are adjusted so as to contain equally 2.2 g/m² of gelatin.

(2) Photographic Processing of the Comparative Sample and Sample of the Present Invention A test piece of the comparative sample 1 prepared in Example 1 and that of the sample 14 of the present invention were wedgewise exposed to light and thereafter, developed at 35° C. for 25 seconds using Developing Solution A described in Example 1, followed by stop, fixation, washing and drying treatments. The thus processed samples were subjected to sensitometry.

Results obtained are shown in Table 4.

TABLE 4

| Remark | Sample No. | Relative Sensitivity | Maximum Density | Gamma | Fog Value |
|---|---|---|---|---|---|
| Comparison | 1 | 100 | 0.8 | 0.4 | 0.05 |
| Present Invention | 14 | 260 | 2.8 | 3.1 | 0.02 |

(The relative sensitivity was expressed taking the sensitivity of Sample No. 1 as 100)

As can be seen from Table 4, the sample 14 of the present invention which had a layer structure different from that of the sample 7 described in Example 1 can also exhibit high sensitivity and provide images of high contrast and high maximum density by development using Developing Solution A. That is, the present invention has turned out to be effective, irrespective of layer structure.

EXAMPLE 5

Two test pieces of the comparative sample 1 prepared in Example 1 were developed at 35° C. for 25 seconds using Developing Solution A and Developing Solution D respectively, which Developing Solution D was prepared by adding the illustrated compound III-1 in a concentration of $1.7 \times 10^{-3}$ mole/l and the illustrated compound I-12 in a concentration of $2 \times 10^{-2}$ mole/l to Developing Solution A. Then, each of them was subjected to stop, fixation, washing and drying treatments, followed by sensitometry. Results obtained were shown in Table 5.

TABLE 5

| Remark | Sample No. | Developing Solution | Relative Sensitivity | Maximum Density | Gamma | Fog Value |
|---|---|---|---|---|---|---|
| Comparison | 1 | Developing Solution A | 100 | 0.8 | 0.4 | 0.05 |
| Present Invention | 1 | Developing Solution A + III-1 ($1.7 \times 10^{-3}$ mol/l) + I-12 ($1 \times 10^{-2}$ mol/l) | 200 | 2.7 | 2.0 | 0.03 |

(Relative sensitivity is expressed taking the sensitivity obtained by development using Developing Solution A as 100)

As can be seen from Table 5, images of high maximum density can also be obtained with high sensitivity and high contrast in the case that the illustrated compound III-1 and I-12 are present in the developing solution. That is, the effect of the present invention can be acquired if only both the mercaptoazaindenes and at least one compound of the general formula (I) or (II) are present at the time of development, in a film or in a developing solution.

While the invention has been described in detail and with reference to specific embodiments thereof, it will be apparent to one skilled in the art that various changes and modifications can be made therein without departing from the spirit and scope thereof.

What is claimed is:

1. A method for surface development-processing a silver halide photographic material containing a surface latent image light-sensitive silver halide emulsion and an internally fogged silver halide emulsion, in which the surface development-processing is carried out in the presence of at least one compound selected from the group consisting of compounds represented by the general formulae (I) and (II) and at least one azaindene having a mercapto group:

wherein $R_1$ and $R_2$ each represents a hydrogen atom, a substituted or unsubstituted alkyl group, a substituted or unsubstituted aryl group, or a substituted or unsubstituted heterocyclic group; $R_3$ and $R_3'$ each represents a substituted or unsubstituted alkylene group, a substituted or unsubstituted arylene group, and a substituted or unsubstituted divalent heterocyclic group; X represents

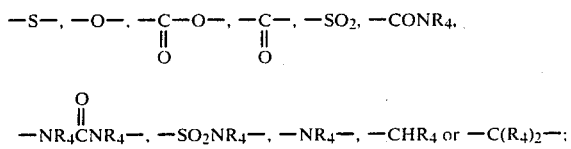

$R_4$ represents a hydrogen atom or $-\!\!+\!\!R_5-\!Y\}_mR_5'-\!R_6$; $R_5$ and $R_5'$ have the same meanings as $R_3$ and $R_3'$; $R_6$ has the same meaning as $R_1$ and $R_2$; Y represents

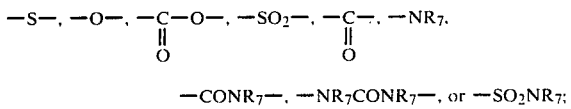

$R_7$ has the same meaning as $R_1$ and $R_2$; l represents 0 or 1, n represents an integer of 1 to 110, and m represents an integer of 0 to 10, wherein when m and n each is not less than 2, X, Y, $R_3$ and $R_5$ may be different between repeating units respectively and at least one X therein must be a sulfur atom:

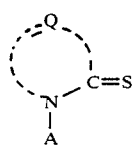 (II)

wherein Q represents atoms necessary to form a heterocyclic ring which may be substituted, and A represents a substituted or unsubstituted alkyl group, or a substituted or unsubstituted aryl group, wherein said azaindene is selected from the group consisting of tetrazaidenes, triazaidenes, pentazaindenes, and purines, and wherein said compounds represented by formula (II) are other than said at least one azaidene having a mercapto group.

2. A method for development-processing as claimed in claim 1, wherein said heterocyclic group for $R_1$ and $R_2$ contains at least one heteroatom selected from the group consisting of sulfur, nitrogen and oxygen atoms.

3. A method for development-processing as claimed in claim 2, wherein said heterocyclic group is a group selected from the group consisting of

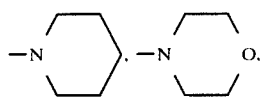

imidazole, benzimidazole, oxazole, benzoxazole, thiazole, benzothiazole, triazole, benzotriazole, pyridine, pyrazine, quinoline, triazine, tetrazole, azaindenes, purine, thiadiazole and oxadiazole.

4. A method for development-processing as claimed in claim 1, wherein said substituted $R_1$, $R_2$, $R_3$, $R_3'$, $R_5$, $R_5'$, $R_6$, $R_7$ and Q are substituted with at least one group selected from the group consisting of a hydroxyl group, a halogen atom, an alkyl group, an aryl group, an amino group, mono- or di-alkyl substituted amino group, —COOH, —COOM and —SO$_3$M, wherein M represents Na or K.

5. A method for development-processing as claimed in claim 1, wherein said arylene group for $R_3$ and $R_3'$ is a group selected from the group consisting of

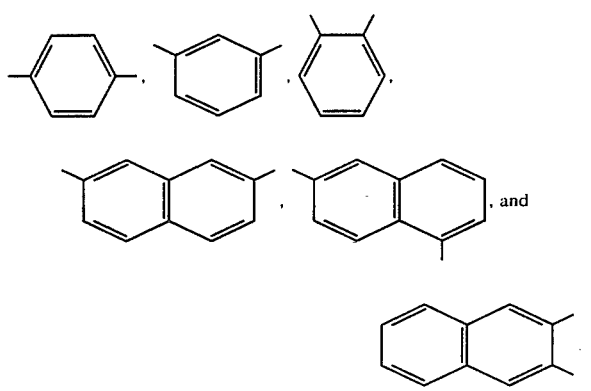

6. A method for development-processing as claimed in claim 1, wherein said heterocyclic group for $R_3$ and $R_3'$ is a group selected from the group consisting of

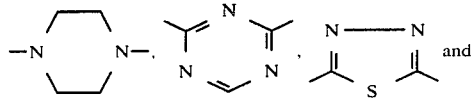

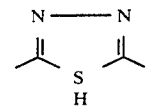

7. A method for development-processing as claimed in claim 1, wherein said heterocyclic ring for Q is a ring selected from the group consisting of thiazoline-2-thione rings, benzothiazoline-2-thione rings, thiazolidine-2-thione rings, imidazolidine-2-thione rings, selenazolidine-2-thione rings, 1,3,4-thiadiazoline-2-thione rings, 1,3,4-selenadiazoline-2-thione rings, 4-selenazoline-2-thione rings, 1,2-dihydropyridine-2-thione rings, benzoxazoline-2-thione rings, benzimidazoline-2-thione rings, benzoselenazoline-2-thione rings, 1,2-dihydroquinoline-2-thione rings, and rhodanine rings.

8. A method for development-processing as claimed in claim 1, wherein said substituted alkyl group for A is substituted with at least one group selected from the group consisting of a hydroxy group, an aryl group, a morpholino group, an alkyl thio group and a hydroxy alkylthio group.

9. A method for development-processing as claimed in claim 1, wherein said substituted aryl group for A is substituted with at least one group selected from the group consisting of an alkyl group, an alkoxy group, an alkylthio group, a hydroxy alkylthio group and a halogen atom.

10. A method for development-processing as claimed in claim 1, wherein said azaindene is a compound selected from the group consisting of the general formula (IIIa) to (IIIf):

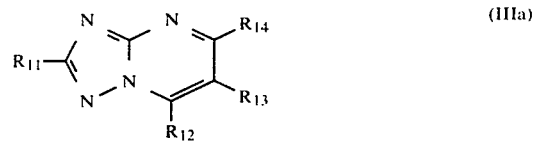 (IIIa)

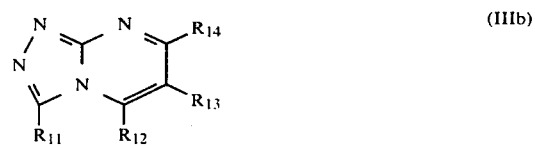 (IIIb)

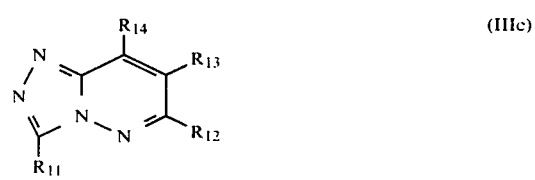 (IIIc)

-continued

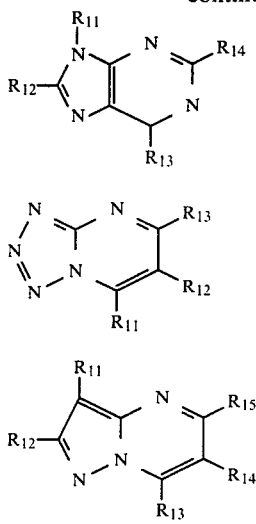

wherein said $R_{11}$ to $R_{15}$ each represents a hydrogen atom, an alkyl group, an aryl group, an aralkyl group, an amino group, hydroxyl group, an alkoxy group, an alkoxycarbonyl group, cyano group and mercapto group; and that, at least one mercapto group must be contaied in the compound represented by general formulae (IIIa) to (IIIf), two of said substituents $R_{11}$ to $R_{15}$ may combine with each other and form a ring, said alkyl group, aryl group, aralkyl group, amino group, alkoxy group may be substituted with at least one group selected from the group consisting an amino group, a substituted amino group, hydroxyl group, an alkoxyl group and alkyl mercapto group.

11. A method for development-processing as claimed in claim 1, wherein at least one compound selected from the group consisting compounds represented by the general formulae (I) and (II) is incorporated in the photographic material.

12. A method for development-processing as claimed in claim 11, wherein said compound is incorporated in an amount of $1 \times 10^{-5}$ to $1 \times 10^{-1}$ mole per mole of the silver halide in the material.

13. A method for development-processing as claimed in claim 1, wherein at least one compound selected from the group consisting compounds represented by the general formulae (I) and (II) is incorporated in a processing solution.

14. A method for development-processing as claimed in claim 13, wherein said processing solution is a developing solution or a solution of a prebath.

15. A method for development-processing as claimed in claim 13, wherein said compound is incorporated in a processing solution in an amount of $10^{-5}$ to $10^{-1}$ mole/l.

16. A method for development-processing as claimed in claim 1, wherein at least one azaindene compound is incorporated in the photographic material.

17. A method for development-processing as claimed in claim 11, wherein said azaindene compound is incorporated in an amount of $1 \times 10^{-5}$ to $1 \times 10^{-1}$ mole per mole of the internally fogged silver halide in the material.

18. A method for development-processing as claimed in claim 1, wherein at least one azaindene compound is incorporated in a processing solution.

19. A method for development-processing as claimed in claim 18, wherein said processing solution is a developing solution or a solution of a prebath.

20. A method for development-processing as claimed in claim 18, wherein said azaindene compound is incorporated in a processing solution in an amount of $10^{-5}$ to $10^{-1}$ mole/l.

21. A method for development-processing as claimed in claim 1, wherein said light-sensitive silver halide and internally fogged silver halide are used in a ratio of from 100:1 to 1:100 by weight.

22. A method for development-processing as claimed in claim 1, wherein the coverage of said light-sensitive silver halide and internally fogged silver halide is 0.5 to 10 g/m² in total of silver.

23. A silver halide photographic material comprising a surface latent image light-sensitive silver halide emulsion, an internally fogged silver halide emulsion, at least one compound selected from the group consisting of compounds represented by the general formulae (I) and (II) and at least one azaindene having a mercapto group:

$$R_1 \!\!+\!\! (R_3)_l X \!\!+\!\!_n R_3{'} \!-\! R_2 \tag{I}$$

wherein $R_1$ and $R_2$ each represents a hydrogen atom, a substituted or unsubstituted alkyl group, a substituted or unsubstituted aryl group, or a substituted or unsubstituted heterocyclic group; $R_3$ and $R_3'$ each represents a substituted or unsubstituted alkylene group, a substituted or unsubstituted arylene group, and a substituted or unsubstituted divalent heterocyclic group; X represents

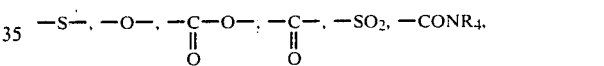

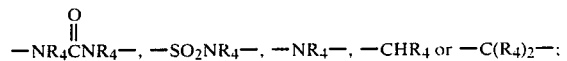

$R_4$ represents a hydrogen atom or $+R_5\!-\!Y\!\!+\!\!_m R_5'\!-\!R_6$; $R_5$ and $R_5'$ have the same meanings as $R_3$ and $R_3'$; $R_6$ has the same meaning as $R_1$ and $R_2$; Y represents

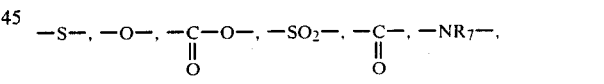

$R_7$ has the same meaning as $R_1$ and $R_2$; l represents 0 or 1, n represents an integer of 1 to 110, and m represents an integer of 0 to 10; wherein when m and n each is not less than 2, X, Y, $R_3$ and $R_5$ may be different between repeating units respectively and that, at least one X therein must be a sulfur atom:

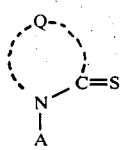

(II)

wherein Q represents atoms necessary to form a heterocyclic ring which may be substituted, and A represents a substituted or unsubstituted alkyl group, or a substituted or unsubstituted aryl group, wherein said azaindene is selected from the group consisting of tetrazaidenes, triazaidenes, pentazaindenes, and purines, and wherein said compounds represented by formula (II) are other than said at least one azaindene having a mercapto group.

24. A method for development-processing as claimed in claim 1, wherein said surface latent image light-sensitive silver halide emulsion has a sensitivity greater than that of the internally fogged silver halide emulsion.

25. A method for development-processing as claimed in claim 1, wherein said surface latent image light-sensitive silver halide emulsion has a sensitivity 10 times or more greater than that of the internally fogged silver halide emulsion.

26. A method for development-processing as claimed in claim 1, wherein the ratio of the content of said surface latent image light-sensitive silver halide emulsion to the content of said internally fogged silver halide emulsion is 100:1 to 1:100 (by weight).

* * * * *